US009539221B2

(12) United States Patent
Bond

(10) Patent No.: US 9,539,221 B2
(45) Date of Patent: *Jan. 10, 2017

(54) METHOD OF TREATING AIRWAY DISEASES WITH β-ADRENERGIC INVERSE AGONISTS

(75) Inventor: Richard A. Bond, Houston, TX (US)

(73) Assignees: EGB ADVISORS, LLC, Wilmington, DE (US); INVION, INC., Melbourne (AU)

(*) Notice: Subject to any disclaimer, the term of this patent is extended or adjusted under 35 U.S.C. 154(b) by 1804 days.

This patent is subject to a terminal disclaimer.

(21) Appl. No.: 10/574,677

(22) PCT Filed: Oct. 8, 2004

(86) PCT No.: PCT/US2004/033157
§ 371 (c)(1),
(2), (4) Date: Jun. 19, 2008

(87) PCT Pub. No.: WO2005/034871

PCT Pub. Date: Apr. 21, 2005

(65) Prior Publication Data

US 2008/0254022 A1    Oct. 16, 2008

Related U.S. Application Data

(60) Provisional application No. 60/510,250, filed on Oct. 10, 2003, provisional application No. 60/555,797, filed on Mar. 23, 2004.

(51) Int. Cl.
| | | |
|---|---|---|
| *A61K 39/395* | (2006.01) | |
| *A61K 31/138* | (2006.01) | |
| *A61K 31/137* | (2006.01) | |
| *A61K 31/192* | (2006.01) | |
| *A61K 31/403* | (2006.01) | |
| *A61K 31/46* | (2006.01) | |
| *A61K 31/47* | (2006.01) | |
| *A61K 31/522* | (2006.01) | |
| *A61K 31/56* | (2006.01) | |

(52) U.S. Cl.
CPC .......... *A61K 31/138* (2013.01); *A61K 31/137* (2013.01); *A61K 31/192* (2013.01); *A61K 31/403* (2013.01); *A61K 31/46* (2013.01); *A61K 31/47* (2013.01); *A61K 31/522* (2013.01); *A61K 31/56* (2013.01)

(58) Field of Classification Search
CPC ...... A61K 31/138; A61K 31/47; A61K 31/46; A61K 31/522; A61K 31/137; A61K 31/192; A61K 31/56; A61K 31/403
USPC .................. 514/171, 411, 657; 424/131.1
See application file for complete search history.

(56) References Cited

U.S. PATENT DOCUMENTS

| 4,428,926 A | 1/1984 | Keith |
|---|---|---|
| 4,769,372 A | 9/1988 | Kreek |
| 5,116,867 A | 5/1992 | Klein et al. |
| 5,316,759 A | 5/1994 | Rose et al. |
| 5,352,680 A | 10/1994 | Portoghese et al. |
| 5,472,943 A | 12/1995 | Crain et al. |
| 5,580,876 A | 12/1996 | Crain et al. |
| 5,585,348 A | 12/1996 | Crain et al. |
| 5,597,699 A | 1/1997 | Lansara |
| 5,624,932 A | 4/1997 | Qin et al. |
| 5,767,125 A | 6/1998 | Crain et al. |
| RE36,547 E | 2/2000 | Crain et al. |
| 6,039,980 A | 3/2000 | Baichwal |
| 6,096,756 A | 8/2000 | Crain et al. |
| 6,107,324 A | 8/2000 | Behan et al. |
| 6,140,509 A | 10/2000 | Behan et al. |
| 6,150,393 A | 11/2000 | Behan et al. |
| 6,194,382 B1 | 2/2001 | Crain et al. |
| 6,218,402 B1 | 4/2001 | Chalmers et al. |
| 6,284,800 B1 | 9/2001 | Broder et al. |
| 6,362,194 B1 | 3/2002 | Crain et al. |
| 6,395,705 B2 | 5/2002 | Crain et al. |
| 6,420,541 B1 | 7/2002 | Behan et al. |
| 6,420,563 B1 | 7/2002 | Beeley et al. |
| 6,541,209 B1 | 4/2003 | Behan et al. |
| 6,555,339 B1 | 4/2003 | Liaw et al. |
| 6,593,094 B2 | 7/2003 | Lansara et al. |
| 6,653,086 B1 | 11/2003 | Behan et al. |
| 6,673,558 B1 | 1/2004 | Lansara |
| 6,737,400 B2 | 5/2004 | Crain et al. |
| 6,740,634 B1 | 5/2004 | Saikawa et al. |
| 6,765,010 B2 | 7/2004 | Crain et al. |

(Continued)

FOREIGN PATENT DOCUMENTS

| WO | WO 98/38985 | 9/1998 |
|---|---|---|
| WO | WO 02/24198 | 4/2002 |
| WO | WO 2004/110551 | 12/2004 |

OTHER PUBLICATIONS

Milligan et al (TIPS, 1997, 18(12), 468-474).*
Bond et al., "Effects of Chronic Treatment with •-Adrenoceptor Antagonist and Inverse Agonists on a Murine Model of Asthma," FASEB J. 17: Abstract No. 142.8 (2003).
T. Costa & A. Herz, "Antagonists with Negative Intrinsic Activity at • Opioid Receptors Coupled to GTP-Binding Proteins," Proc. Natl. Acad. Sci. USA 86: 7321-7325 (1989).
R.A. De Ligt et al., "Inverse Agonism at G Protein-Coupled Receptors: (Patho)physiological Relevance and Implications for Drug Discovery," Br. J. Pharmacol. 130: 1-12 (2000).

(Continued)

*Primary Examiner* — Jeffrey S Lundgren
*Assistant Examiner* — Ibrahim D Bori
(74) *Attorney, Agent, or Firm* — Ditthavong & Steiner, P.C.

(57) ABSTRACT

The use of β-adrenergic inverse agonists provides a new and highly efficient way of treating a number of pulmonary airway diseases, including asthma, emphysema, and chronic obstructive pulmonary diseases. In general, such a method comprises administering a therapeutically effective amount of a β-adrenergic inverse agonist to the subject to treat the pulmonary airway disease. Particularly preferred inverse agonists include nadolol and carvedilol.

18 Claims, 9 Drawing Sheets

(56) References Cited

U.S. PATENT DOCUMENTS

| | | | |
|---|---|---|---|
| 6,806,054 B2 | 10/2004 | Lehmann-Bruinsma et al. | |
| 7,026,329 B2 | 4/2006 | Crain et al. | |
| 2001/0006967 A1 | 7/2001 | Crain et al. | |
| 2002/0094947 A1 | 7/2002 | Crain et al. | |
| 2002/0137761 A1 | 9/2002 | Crain et al. | |
| 2002/0187990 A1* | 12/2002 | Parks et al. | 514/269 |
| 2004/0249416 A1 | 12/2004 | Yun et al. | |
| 2005/0021092 A1 | 1/2005 | Yun et al. | |

OTHER PUBLICATIONS

G. Milligan et al., "Inverse Agonism: Pharmacological Curiosity or Potential Therapeutic Strategy?," Trends Pharmacol. Sci. 16: 10-13 (1995).

Z. Callaerts-Vegh et al., "Effects of Acute and Chronic Administration of •-Adrenoceptor Ligands on Airway Function . . . ," Proc. Natl. Acad. Sci. USA 101:4948-4953 (2004).

L. Rrubenstein & R. Lansara, "Activation of G Protein-Coupled Receptors Entails Cysteine Modulation of Agonist Binding," J. Molecular Structure (Theochem) 430: 57-71 (1998).

R. Lansara, "Weber's Law Modeled by the Mathematical Description of a Beam Balance," Mathematical Biosciences 122: 89-94 (1994).

A.S.P. Hua et al., "Results from a Multicentre Trial of Metoprolol and a Study of Hypertensive Patients with Chronic . . . ," Med. J. Australia 1978: 282-286 (Mar. 11, 1978).

L. Daeffler & Y. Landry, "Inverse Agonism at Heptahelical Receptors: Concept, Experimental Approach and Therapeutic Potential," Fundam. Clin. Pharmacol. 14: 73-87 (2000).

R. Lanzara, "Preventing Rapid Receptor Desensitization at the beta-1-Adrenergic . . . " The Chemweb Preprint Server, http://preprint.che.chemweb.com/medichem/0302002 (2003).

R. Lanzara, "Desensitization of a Balance with Langmuir Binding of Weights" arXiv, http://arXiv.org/abs/physics/0303055 (2003).

R. Lanzara, "The Anemone and the Balance" The Chemweb Preprint Server 2003, http://preprint.chemweb.com/chemistry/0302001: (2003).

A.-M. Taburet & B. Schmit, "Pharmacokinetic Optimisation of Asthma Treatment," Clin. Pharmacokinet. 26: 396-418 (1994).

S. Markowitz & J.D. Morin, "Timolol: a 4-Year Follow-Up Study," Can. J. Ophthalmol. 18: 278-280 (1983).

R. Seifert & K. Wenzel-Seifert, "Constitutive Activity of G-Protein-Coupled Receptors: Cause of Disease and . . . ," Naunyn-Schmiedeberg's Arch. Pharmacol. 366:381-416 (2002).

C. Ellis, "Timing Is Everything," Nature Rev. Drug Discovery 3: 387 (2004).

H. Krum et al., "Baseline Predictors of Tolerability to Carvedilol in Patients with Chronic Heart Failure," Heart 84: 615-619 (2000).

S. Nagaraja et al., "Treatment with Inverse Agonists Enhances Baseline Atrial Contractility in Transgenic Mice with . . . ," Br. J. Pharmacol. 127:1099-1104 (1999).

S.R. Salpeter, "Cardiovascular Effects of •-Agonists in Patients with Asthma and COPD: A Meta-Analysis," Chest 125: 2309-2321 (2004).

R. Newcomb et al., "Rebound Hyperresponsiveness to Muscarinic Stimulation After Chronic Therapy with an Inhaled Muscarinic . . . ," Am. Rev. Respir. Dis. 132: 12-15 (1985).

H.J. Van Der Woude et al., "Detrimental Effects of •-Blockers in COPD: A Concern for Nonselective •-Blockers," Chest 127: 818-824 (2005).

"Interleukin-10 Regulation in Normal Subjects and Patients with Asthma," J. Allerg. Clin. Immunol. 97: 1288-1296 (1996).

A publication, prescribing information for Coreg (carvedilol), GlaxoSmithKline, Research Triangle Park, NC 27709, Oct. 2003.

A publication, a package insert for Corgard tablets (nadolol), Monarch Pharmaceuticals, Bristol, TN 37620, Oct. 2001.

A publication, prescribing information for Inderal (propranolol hydrochloride), Wyeth Pharmaceuticals Inc., Philadephia, PA 19101, Aug. 2006.

R.S. McNeill, "Effect of a •-Adrenergic-Blocking Agent, Propranolol, on Asthmatics," The Lancet (Nov. 21, 1964), pp. 1101-1102.

J.M Raine et al., "Near-Fatal Bronchospasm After Oral Nadolol in a YoungAsthmatic and Response to Ventilation With Halothane," Brit. Med. J. 282: 548-549 (1981).

A publication, prescribing information for Sterile Ophthalmic Gel Forming Solution Timoptic-XE (timolol maleate), Merck & Co., Whitehouse Station, NJ 08889, Mar. 2001.

* cited by examiner

METHOD OF TREATING AIRWAY DISEASES WITH β-ADRENERGIC INVERSE AGONISTS

CROSS-REFERENCES

This application claims priority from Provisional Application Ser. No. 60/510,250, by Richard A. Bond, entitled "Method for Treating Airway Diseases with Beta-Adrenergic Inverse Agonists," filed Oct. 9, 2003, which is incorporated herein in its entirety by this reference.

STATEMENT REGARDING FEDERAL FUNDED RESEARCH

Certain of the research leading to the invention recited in this application has been funded by grants from the National Institutes of Health. The United States government may therefore have certain rights in this invention.

BACKGROUND OF THE INVENTION

The present invention relates to novel methods for preventing, treating, or reducing the severity of diseases and conditions mediated by β-adrenergic receptors, particularly pulmonary airway diseases. In particular, it provides for methods and compositions for treating pulmonary airway diseases by long-term administration of β-adrenergic inverse agonist drugs, either alone or in combination with other drugs, such as $\beta_2$-agonists, steroids, leukotriene modifiers, anticholinergics, methylxanthines, phosphodiesterase-4 inhibitors, or anti-IgE antibodies.

Many diseases and conditions are mediated by β-adrenergic receptors. In particular, these receptors are involved in many pulmonary airway diseases. Pulmonary airway diseases are characterized by reduced pulmonary function and airway flow. These symptoms are often due to secretion of mucus or tissue damage. These diseases include allergic rhinitis ("hay fever"), asthma, cystic fibrosis, chronic obstructive pulmonary disease (COPD), Churg-Strauss syndrome, bronchitis, bronchiectasis, and emphysema. These diseases are serious and are responsible for significant mortality and morbidity.

COPD patients have obstructed airflow in the lungs. There are a number of ways that patients develop COPD. However, the hallmark of the disorder is dyspnea, or breathlessness. COPD is frequently associated with long-term cigarette smoking and can develop as the result of untreated allergic conditions. The aging process can also cause the bronchi and bronchioles to lose their elasticity.

Churg-Strauss syndrome is an inflammatory disease in which patients exhibit asthmatic symptoms such as airway hyperreactivity. Inflammation of pulmonary airways occurs, compromising pulmonary function.

In bronchitis, airway function is compromised due to hypersecretion of mucus, initially due to irritants. Bronchitis can be the result of infection or allergic reaction. With chronic bronchitis, coughing is persistent but may no longer be sufficient to clear airways, leading to airflow obstruction. Chronic bronchitis affects the bronchial tubes.

Bronchiectasis results from infection in the lungs, leading to irreversible airway damage. Patients often complain of persistent cough and expectorate a foul-smelling sputum. The consequences of the infection, in conjunction with the secretions, contributes to airway obstruction despite the fact that bronchi and bronchioles can be exceptionally dilated.

Patients with emphysema have reduced pulmonary function due to destructive damage of the walls of lung alveoli. Often, patients are long-time smokers and have elevated levels of inflammatory cells, such as neutrophils and macrophages, in the lungs; other pathophysiologic processes are at work as well. The smoke is believed to activate lung neutrophils to release elastase, a damaging proteolytic enzyme. Other environmental irritants can also be involved in emphysema.

Asthma alone is a chronic problem for 20 million Americans patients. The rate of occurrence of asthma has been increasing rapidly in the United States, particularly in urban areas, and particularly in children. The cause of this increase is not known, but exposure to environmental pollutants is suspected. The age-adjusted mortality rate for asthma in the United States increased 55.6% between 1979 and 1998 (American Lung Association's Epidemiology and Statistics Unit, Best Practices and Program Services. Trends in Asthma Morbidity and Mortality, 2002). Persons suffering from asthma are often sensitive to allergens, such as household dust, animal dander, and pollen (allergic asthma). However, intrinsic asthma can be triggered in a patient by emotional distress or panic, as well as by factors such as exposure to cold or exercise, or by administration of certain medications such as aspirin. In asthma, patients exhibit airway hyperresponsiveness to these provocations. These trigger immune system cells to release histamines, IgE molecules, cytokines, or chemokines. Airway smooth muscle responds acutely to these provocations, resulting in bronchial constriction. Additionally, the airway becomes damaged and inflamed, and mucus is secreted, further limiting airway flow. Asthma attacks are characterized by shortness of breath, caused by contraction of the smaller bronchi and bronchioles, chest tightness, coughing, and wheezing. The attacks can be mild, moderate, or severe.

Patients with these airway disorders may have airway spasms, further reducing airflow through the pulmonary tree. During an attack, a patient's airway is constricted, leading to difficulty breathing. Airway smooth muscle is responsible for the bronchoconstriction. The airway smooth muscle cells express $\beta_2$-adrenergic receptors. Agonist binding to these receptors, such as by epinephrine or other $\beta_2$-agonist drugs, results in smooth muscle relaxation.

Consequently, for acute bronchospasms many patients inhale short-acting $\beta_2$-adrenergic agonists to prevent or reduce the severity of asthma attacks.

However, chronic administration of $\beta_2$-adrenergic agonists has been demonstrated to lead to drug tolerance and reduced therapeutic effect on their continued administration. Reduced responsiveness, also known as tachyphylaxis or tolerance, results from a culmination of events, which include desensitization, sequestration, and down-regulation of receptors. Furthermore, there is also an increased hyperresponsiveness of the pulmonary airway in response to provocations such as allergens.

Epidemiological studies have demonstrated a positive correlation between the chronic use of short-acting $\beta_2$-adrenergic agonists and asthma mortality. A large trial with the long-acting $\beta_2$-adrenergic agonist, salmeterol, was stopped due to increased death rates. This underscores that, while short-term administration of $\beta_2$-adrenergic agonists may be helpful to asthmatic patients and to patients with other diseases and conditions modulated by $\beta_2$-adrenergic receptors, long-term administration of these agonists may be deleterious.

Conventional wisdom in the management of asthma and other diseases and conditions in which airway hyperresponsiveness and bronchoconstriction occur is that the administration of beta blockers, such as those that are frequently used in the treatment of cardiovascular conditions, are definitely contraindicated for asthmatic patients. In T. Clark & J. Rees, "Practical Management of Asthma" (2d ed, Martin Dunitz, 1996), it states: "These (β-blockers) often produce adverse effects when given to asthmatics, Treatment with beta blockers can also bring to light previously undiagnosed asthma. Fatal bronchoconstriction has been produced by a single dose of beta blockers. It is best to avoid all beta blockers in asthmatics."

Therefore, there needs to be increased focus on the bronchoconstriction occurring in asthma. This can progress to status asthmaticus. More efficient and long-lasting therapeutic modalities that can reverse the bronchoconstriction and can bring about dilation of the airways are needed.

Consequently, there is a tremendous need for new therapeutic alternatives to $β_2$-adrenergic agonist use in asthmatics and in patients suffering from other diseases and conditions modulated by $β_2$-adrenergic receptors, particularly diseases affecting the respiratory system such as asthma.

SUMMARY OF THE INVENTION

One embodiment of the invention is a method for treatment of pulmonary airway disease in a subject suffering from pulmonary airway disease comprising administering a therapeutically effective amount of a β-adrenergic inverse agonist to the subject to treat the pulmonary airway disease.

Particularly preferred inverse agonists are nadolol, carvedilol, metoprolol, timolol, and ICI 118,551.

The pulmonary airway disease can be selected from the group consisting of asthma, bronchiectasis, bronchitis, chronic obstructive pulmonary disease, Churg-Strauss syndrome, the pulmonary sequelae of cystic fibrosis, emphysema, allergic rhinitis, and pneumonia.

In this method, the β-adrenergic inverse agonist can be administered over time in a series of graduated doses starting with the lowest dose and increasing to the highest dose.

Another aspect of the invention is a pharmaceutical composition comprising:
(1) nadolol in a quantity selected from the group consisting of 1 mg, 3 mg, 5, mg, 10 mg, 15 mg, 30 mg, 50 mg, and 70 mg; and
(2) a pharmaceutically acceptable carrier.

Yet another aspect of the invention is a blister pack comprising:
(1) a lower substrate;
(2) an intermediate dosage holder that is shaped to generate a plurality of cavities and that is placed over the lower substrate, the cavities being shaped to hold dosage forms of a β-adrenergic inverse agonist;
(3) an upper substrate placed over the intermediate dosage holder that has a plurality of apertures, each aperture being located to accommodate a corresponding cavity; wherein the dosage forms are of graduated dosages starting with a lowest dose and proceeding to a highest dose; and
(4) dosage forms of a β-adrenergic inverse agonist placed in the cavities.

Yet another aspect of the invention is a blister pack comprising:
(1) a lower substrate;
(2) an intermediate dosage holder that is shaped to generate a plurality of cavities, the cavities being shaped to hold dosage forms of a β-adrenergic inverse agonist;
(3) an upper substrate placed over the intermediate dosage holder that has a plurality of apertures, each aperture being located to accommodate a corresponding cavity; and
(4) dosage forms of a β-adrenergic inverse agonist placed in the cavities, wherein the dosage forms are of at least two dosages of a β-adrenergic inverse agonist: (i) a maintenance dose that is the highest dose in a series of graduated doses; and (ii) at least one backup restoration dose or a lower dose to be taken in a specified condition.

Still another aspect of the invention is a method for treatment of pulmonary airway disease in a subject suffering from pulmonary airway disease comprising administering to the subject: (1) a therapeutically effective amount of a β-adrenergic inverse agonist and (2) a therapeutically effective amount of a $β_2$-selective adrenergic agonist in order to treat the pulmonary airway disease.

Still another aspect of the invention is a method for treatment of pulmonary airway disease in a subject suffering from pulmonary airway disease comprising administering to the subject: (1) a therapeutically effective amount of a β-adrenergic inverse agonist and (2) a therapeutically effective amount of a steroid in order to treat the pulmonary disease.

Still another aspect of the invention is a method for treatment of pulmonary airway disease in a subject suffering from pulmonary airway disease comprising administering to the subject: (1) a therapeutically effective amount of a β-adrenergic inverse agonist and (2) a therapeutically effective amount of an anticholinergic drug in order to treat the pulmonary airway disease.

Still another aspect of the invention is a method for treatment of pulmonary airway disease in a subject suffering from pulmonary airway disease comprising administering to the subject: (1) a therapeutically effective amount of a β-adrenergic inverse agonist and (2) a therapeutically effective amount of a xanthine compound in order to treat the pulmonary airway disease.

Still another aspect of the invention is a method for treatment of pulmonary airway disease in a subject suffering from pulmonary airway disease comprising administering to the subject: (1) a therapeutically effective amount of a β-adrenergic inverse agonist and (2) a therapeutically effective amount of an anti-IgE antibody in order to treat the pulmonary airway disease.

Still another aspect of the invention is a method for treatment of pulmonary airway disease in a subject suffering from pulmonary airway disease comprising administering to the subject: (1) a therapeutically effective amount of a β-adrenergic inverse agonist and (2) a therapeutically effective amount of a leukotriene modifier in order to treat the pulmonary airway disease.

Still another aspect of the invention is a method for treatment of pulmonary airway disease in a subject suffering from pulmonary airway disease comprising administering to the subject: (1) a therapeutically effective amount of a β-adrenergic inverse agonist and (2) a therapeutically effective amount of phosphodiesterase IV inhibitor in order to treat the pulmonary airway disease.

Still another aspect of the invention is a pharmaceutical composition comprising:
(1) a therapeutically effective amount of a β-adrenergic inverse agonist;
(2) a therapeutically effective amount of a second therapeutic agent effective to treat a pulmonary airway disease, the second therapeutic agent being selected from the group consisting of a $β_2$-selective adrenergic agonist, a steroid, an anticholinergic drug, a xanthine compound, an anti-IgE antibody, a leukotriene modifier, and a phosphodiesterase IV inhibitor; and (3) a pharmaceutically acceptable carrier.

Still another aspect of the invention is a blister pack comprising:
(1) a lower substrate;
(2) an intermediate dosage holder that is shaped to generate a plurality of cavities and that is placed over the lower substrate, the cavities being shaped to hold dosage forms of the pharmaceutical composition including both a therapeutic amount of a β-adrenergic inverse agonist and a therapeutic amount of a second therapeutic agent effective to treat a pulmonary airway disease;
(3) an upper substrate placed over the intermediate dosage holder that has a plurality of apertures, each aperture being located to accommodate a corresponding cavity; and
(4) dosage forms of the pharmaceutical composition placed in the cavities.

Yet another aspect of the invention is a blister pack comprising:
(1) a lower substrate;
(2) an intermediate dosage holder that is shaped to generate a plurality of cavities and that is placed over the lower substrate, the cavities being shaped to hold dosage forms of:
(a) a first pharmaceutical composition that comprises: (i) a therapeutically effective amount of a β-adrenergic inverse agonist; and (ii) a first pharmaceutically acceptable carrier; and (b) a second pharmaceutical composition that comprises: (i) a therapeutically effective amount of a second therapeutic agent effective to treat a pulmonary airway disease, the second therapeutic agent being selected from the group consisting of a $β_2$-selective adrenergic agonist, a steroid, an anticholinergic drug, a xanthine compound, an anti-IgE antibody, a leukotriene modifier, and a phosphodiesterase IV inhibitor; and (ii) a second pharmaceutically acceptable carrier;
(3) an upper substrate placed over the intermediate dosage holder that has a plurality of apertures, each aperture being located to accommodate a corresponding cavity; and
(4) dosage forms of the first and second pharmaceutical compositions placed in the cavities.

BRIEF DESCRIPTION OF THE DRAWINGS

The following invention will become better understood with reference to the specification, appended claims, and accompanying drawings, where:

DETAILED DESCRIPTION OF THE INVENTION

Figure 1:
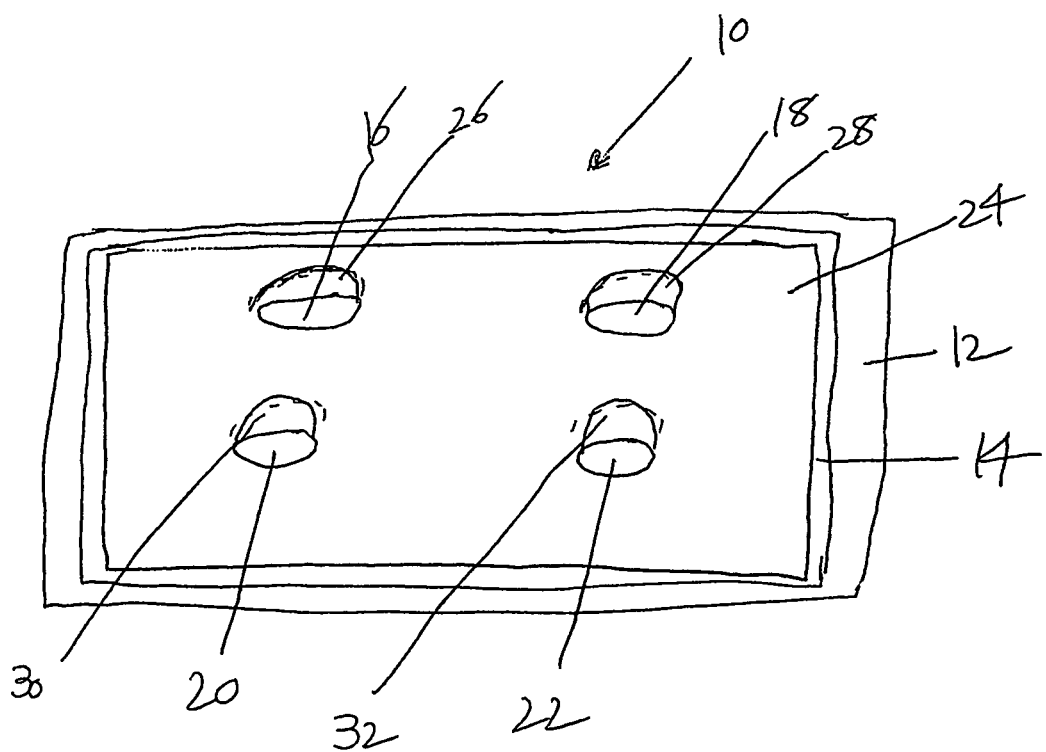
FIG. 1 is a diagram of a blister pack holding dosage forms of inverse agonists according to the invention.

As used herein, in the generally accepted two-state model of receptor theory, the term "agonist" is defined as a substance that has an affinity for the active site of a receptor and thereby preferentially stabilizes the active state of the receptor, or a substance, including, but not limited to, drugs, hormones, or neurotransmitters, that produces activation of receptors and enhances signaling by those receptors. Irrespective of the mechanism or mechanisms of action, an agonist produces activation of receptors and enhances signaling by those receptors.

As used herein, in the two-state model of receptor theory, the term "antagonist" is defined as a substance that does not preferentially stabilize either form of the receptor, active, or inactive, or a substance, including, but not limited to, drugs, hormones, and neurotransmitters, that prevents or hinders the effects of agonists and/or inverse agonists. Irrespective of the mechanism or mechanisms of action, an antagonist prevents or hinders the effects of agonists and/or inverse agonists.

As used herein, in the two-state model of receptor theory, the term "inverse agonist" is defined as a substance that has an affinity for the inactive state of a receptor and thereby preferentially stabilizes the inactive state of the receptor, or a substance, including, but not limited to, drugs, hormones, or neurotransmitters, that produces inactivation of receptors and/or prevents or hinders activation by agonists, thereby reducing signaling from those receptors.

As used herein, the term "concurrent administration" refers to the administration of two or more active agents sufficiently close in time to achieve a combined therapeutic effect that is preferably greater than that which would be achieved by the administration of either agent alone. Such concurrent administration can be carried out simultaneously, e.g., by administering the active agents together in a common pharmaceutically acceptable carrier in one or more doses.

The term "subject," as used herein, refers to human or animal species. In general, methods and compositions according to the present invention can be used to treat not only humans, but also socially or economically important animal species such as cows, horses, sheep, pigs, goats, dogs, and cats. Unless specified, methods and compositions according to the present invention are not limited to treatment of humans.

The term "therapeutically effective amount," as used herein, refers to an amount of a therapeutic agent or composition effective to treat, ameliorate, or prevent a desired disease or condition, or to exhibit a detectable therapeutic or preventative effect. The effect can be detected by, for example, chemical markers, antigen levels, or changes in physiological indicators such as airway resistance. Therapeutic effects also include reduction in physical symptoms, such as decreased bronchoconstriction or decreased airway resistance, and can include subjective improvements in well-being noted by the subjects or their caregivers. The precise therapeutically effective amount for a subject will depend upon the subject's size, weight, and health, the nature and extent of the condition affecting the subject, and the therapeutics or combination of therapeutics selected for administration, as well as variables such as liver and kidney function that affect the pharmacokinetics of administered therapeutics. Thus, it is not useful to specify an exact effective amount in advance. However, the effective amount for a given situation can be determined by routine experimentation and is within the judgment of the clinician.

One embodiment of the invention is a method of treating a disease or condition affected by the modulation of a beta receptor by administering an effective quantity of an inverse agonist for the receptor whose modulation is involved in the disease or condition. Typically, the disease or condition is a respiratory disease or condition, including, but not limited to, asthma, chronic obstructive pulmonary disease (COPD), bronchitis, bronchiectasis, emphysema, allergic rhinitis, the pulmonary sequelae of cystic fibrosis, Churg-Strauss syndrome, and pneumonia.

In classical receptor theory, two classes of G protein-coupled receptor (GPCR) ligands were considered: agonist and antagonist. Receptors were believed to exist in a single quiescent state that could only induce cellular signaling upon agonist binding to produce an activated receptor state. In this model, binding by antagonists produced no cellular signaling but simply prevented receptors from being bound and activated by agonists. Then, Costa and Herz demonstrated that receptors could be manipulated into a constitutive or spontaneously active state that produced cellular signaling in the absence of agonist occupation. They also provided evidence that certain compounds inactivate those spontaneously active receptors (T. Costa & A. Herz, "Antagonists with Negative Intrinsic Activity at 6 Opioid Receptors Coupled to GTP-Binding Proteins," *Proc. Natl. Acad. Sci. USA* 86: 7321-7325 (1989)). There is further evidence that GPCRs exist in constitutively or spontaneously active states that are inactivated to some degree by inverse agonists (R. A. de Ligt et al., "Inverse Agonism at G Protein-Coupled Receptors: (Patho)physiological Relevance and Implications for Drug Discovery," *Br. J. Pharmacol.* 130:1-12 (2000); G. Milligan et al., "Inverse Agonism: Pharmacological Curiosity or Potential Therapeutic Strategy?," *Trends Pharmacol. Sci.* 16:10-13 (2000)).

The basis of the strategy of this embodiment of the invention is the recognition of the existence of inverse agonists and the understanding of the effect that chronic treatment with inverse agonists has on receptor function. What is an inverse agonist and how does it function? Receptors, such as β-adrenergic receptors that respond to adrenalin (epinephrine), typically exist in an equilibrium between two states, an active state and an inactive state. When receptors bind to agonists, such as adrenalin for the β-adrenoceptors, they stop them from cycling back into the inactive state, thus shifting the equilibrium between the active and inactive states according to the Law of Mass Action. This occurs because those receptors bound to agonists are removed from the equilibrium. Typically, antagonists bind to the receptors, but prevent the binding of agonists. However, molecules known as "inverse agonists" bind to the receptors in the inactive state, causing the equilibrium between the active and the inactive state to shift toward the inactive state. This is not merely a matter of blocking agonist binding.

Moreover, there is a population of spontaneously active receptors in vivo. These receptors provide a baseline constitutive level of activity; the activity is never entirely "off."

As indicated above, it has been well demonstrated that chronic administration of β-adrenergic agonists causes agonist-dependent desensitization. Upon acute administration of β-agonists, adrenergic receptors are internalized, thereby preventing them from being restimulated further for pulmonary relaxation. With chronic administration of β-agonists, there is actually a down regulation in the total number of β-adrenergic receptors. The consequence may be the observed loss of responsiveness seen in asthmatic patients on long-acting β-agonists, and referred to as tolerance or tachyphylaxis, as described above.

The treatment methods of the present invention are based on the discovery that a chronic administration of an inverse agonist has the effect of up regulating the population of active β-adrenergic receptors. The observed activity may be due to the receptor's constitutive baseline activity or the combined effect of increased level of receptors responding to endogenous agonists. This leads to the seemingly paradoxical result that the administration of a drug that would appear, at first blush, to degrade a physiological function, such as by causing airway hyperresponsiveness in asthma, can, if administered chronically, enhances that physiological function by up regulating the population of spontaneously active β-adrenergic receptors associated with that physiological function. This is a specific application of the principle of "paradoxical pharmacology."

Along these lines, the use of cardioselective β inverse agonists (those with a preference for the $\beta_1$-adrenergic receptor subtype) has been demonstrated to be safe in hypertensive and congestive heart failure (CHF) patients with chronic airway obstructive pulmonary disease (COPD).

Multiple studies have demonstrated that chronic administration of cardioselective β inverse agonists does not change pulmonary function of CHF patients with COPD or asthma. Forced expiratory volume (FEV), a standard measure of pulmonary function, was essentially unchanged in patients treated with cardioselective β inverse agonists. These data indicate that chronic administration of cardioselective β inverse agonists is safe in CHF patients with pulmonary airway disease. However, these drugs are not preferred for reducing or altering the symptoms of pulmonary airway disease.

In U.S. Pat. No. 5,116,867 to Klein et al., incorporated herein by this reference, D-propranolol or racemic mixtures composed of 85% or more of the D form was proposed for the treatment of asthma. The D-form of propranolol was 1/100 as potent as the L-form in inhibiting the β-adrenergic receptor. In contrast, this patent specifies the use of the active form or of racemic mixtures containing 50% or more of the active β-adrenergic antagonist.

In U.S. Pat. No. 6,284,800 to Broder et al., incorporated herein by this reference, the D forms of propranolol, metoprolol, carvedilol, or bisoprolol were proposed for the treatment of asthma. Experiments were performed comparing the D-form versus the L-form of propranolol, demonstrating that acute administration of D-propranolol was beneficial in inhibiting antigen-induced bronchoconstriction and reducing airway hyperresponsiveness. In contrast, acute administration of the L-form increased specific lung resistance as expected for an active β-adrenergic agonist. The D form of propranolol was inactive with respect to β-adrenergic receptors. Consequently, U.S. Pat. No. 6,284,800 does not deal with inverse agonism.

PCT Patent Publication No. WO 02/29534, by Bond, had proposed compounds with $\beta_1$ and/or $\beta_2$ antagonist activity that inhibited β-adrenergic receptors to treat allergic and inflamatory disorders including asthma and chronic obstructive pulmonary disease. Experiments were performed in which asthmatic mice were chronically treated with compounds characterized as β-antagonists, including alprenolol, carvedilol, and ICI-118,551. Then, tracheas from the mice were excised and contraction of the tracheas in response to methacholine was monitored as a surrogate for an asthma attack. The most effective compound was alprenolol, followed by carvedilol, then ICI-118,551.

More physiologically relevant experiments in asthmatic mice performed by the inventor in the present application have demonstrated that alprenolol, originally thought to be beneficial chronically, does not reduce airway hyperresponsiveness compared to untreated asthmatic mice. Even though alprenolol is a β-adrenergic antagonist, it has partial agonist activity. Carvedilol is a $\beta_1/\beta_2$ non-selective adrenergic antagonist with $\alpha_1$-adrenergic antagonist activity. In the new experiments reported in the present application, chronic administration of carvedilol does reduce airway hyperresponsiveness, which would be beneficial to asthmatics, but it also shifts the sensitivity of the responsiveness to methacholine to lower concentrations, which could be detrimental to asthmatics.

Moreover, in the experiments reported in PCT Patent Publication No. WO 02/29534, tracheas were excised from mice, leaving behind the vast majority of the pulmonary airways. In mice, the trachea contains almost exclusively only $\beta_1$ adrenergic receptors whereas the remainder of the airways is a mixture of $\beta_1$ and $\beta_2$ adrenergic receptors. In contrast, human airways, both the trachea and the smaller airways, contain almost exclusively $\beta_2$ receptors. Consequently, the experiments reported in PCT Patent Publication No. WO 02/29534 have little predictive value for human asthma. The experiments reported in the present application more closely reflect human physiology.

β-adrenergic antagonist drugs or "beta blockers" are treated as having the same activity in conventional pharmacology. Beta blockers are further classified based on their selectivity or lack thereof for either the $\beta_1$ (termed "cardioselective") or $\beta_1/\beta_2$ ("nonselective") or $\beta_2$ selective only. Additionally, beta blockers can be classified as to whether or not they have partial agonist activity or are actually inverse agonists. The latter definition is based on the new appreciation, recited in the present application, that many G-coupled protein receptors, including the β-adrenergic receptors, exhibit low level spontaneous activity that can be further prevented by the binding of the inverse agonists to the receptor. This distinction was not made in PCT Patent Publication No. WO 02/29534, which referred simply to "antagonists."

Despite this knowledge of the subclasses of beta blockers in the field, many scientists have continued to treat compounds from the different subclasses as one class. An example of this is the clinical testing in 1998-1999 of the beta blocker bucindolol for congestive heart failure. Previously, two other beta blockers, metoprolol and carvedilol, had been clinically tested and demonstrated significant mortality reduction in patients with CHF. Bucindolol failed to demonstrate any benefit over placebo, and thus clinical testing was discontinued. The inventor of the present application notes that both metoprolol and carvedilol are β-inverse agonists whereas bucindolol is a neutral antagonist with partial agonist activity. Consequently, the inventor of the present application would predict that only β-adrenergic inverse agonists would be effective in treatment of CHF. In the same vein, the inventor of the present application predicts that only β-adrenergic inverse agonists will be effective for chronic treatment of asthma airway hyperresponsiveness. This distinction is not made or suggested in PCT Patent Publication No. WO 02/29534.

Instead, this invention provides for the use of the active β-adrenergic receptor binding forms of β-adrenergic inverse agonists in the treatment of asthma, COPD, and other diseases that are marked by airway hyperresponsiveness, including, but not limited to, emphysema, Churg-Strauss syndrome, bronchitis, and bronchiectasis. The inverse agonists can be in pure or substantially pure enantiomeric or diastereomeric form or can be racemic mixtures. In many cases, the active form of such compounds is the L form when there is only one chiral center. In the case of nadolol, which has three chiral centers and potentially 12 isomers, though, typically, only two are formed during synthesis, the most active form is the RSR form of nadolol.

Especially preferred for use according to the invention are the β-adrenergic inverse agonists: nadolol, e.g., as the hydrochloride: bupranolol, e.g., as the hydrochloride; butoxamine, e.g., as the hydrochloride; carazolol, e.g., as the hydrochloride; carvedilol; e.g., as the hydrochloride; ICI-118,551, i.e., as the hydrochloride; levobunolol, e.g., as the hydrochloride; metoprolol, as the tartrate or succinate; propranolol, e.g., as the hydrochloride; sotalol, e.g., as the hydrochloride; timolol; e.g., as the hydrochloride; and the salts, solvates, analogues, congeners, bioisosteres, hydrolysis products, metabolites, precursors, and prodrugs thereof. Particularly preferred inverse agonists are carvedilol and nadolol. A most particularly preferred inverse agonist is nadolol. As used herein, the recitation of an inverse agonist compound, or, where appropriate, an agonist compound, includes all pharmaceutically acceptable salts of that inverse agonist compound or agonist compound unless excluded. Thus, the recitation of nadolol as the hydrochloride does not exclude other pharmaceutically acceptable salts that have been prepared or that can be prepared.

The inverse agonists useful in methods and compositions according to the invention typically display inverse agonism to $\beta_2$-adrenergic receptors; either as non-selective inverse agonists that display inverse agonism to both the $\beta_1$- and $\beta_2$-adrenergic receptors or as a selective $\beta_2$-inverse agonist.

Preferably, inverse agonists useful in methods and compositions according to the invention both reduce airway hyperresponsiveness and, when tested in the asthmatic mouse model, do not shift the methacholine response to the left (i.e., to lower methacholine concentrations).

Specifically, also expected to be within the scope of the invention are analogues of nadolol of formula (I) wherein $R_1$ is hydrogen or lower alkyl, $R_2$ is hydrogen or lower alkyl, and m and n are 1 to 3, with the proviso that where $R_1$ and $R_2$ are both hydrogen and m is 1, n is other than 1. As used herein, the term "lower alkyl" is defined as a straight or branched hydrocarbyl residue of 1-6 carbon atoms.

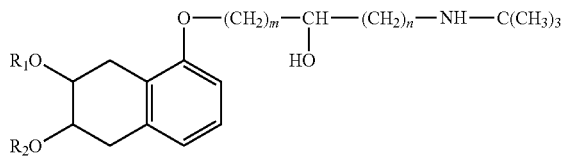

(I)

Also specifically expected to be within the scope of the invention are analogues of carvedilol of formula (II) wherein $R_1$ is hydrogen or lower alkyl, $R_2$ is hydrogen or lower alkyl, and $R_3$ is hydrogen or lower alkyl, with the proviso that all of $R_1$, $R_2$, and $R_3$ are not all hydrogen.

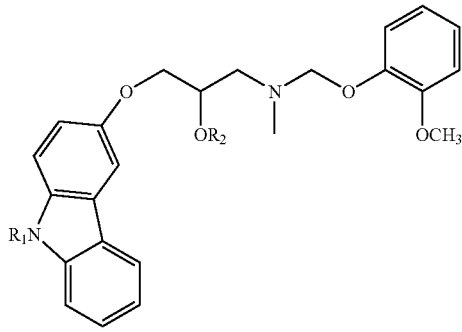

(II)

Also expected to be within the scope of the invention are analogues of timolol of formula (III) wherein $R_1$ is hydrogen or lower alkyl and $R_2$ is hydrogen or lower alkyl, with the proviso that both $R_1$ and $R_2$ are not hydrogen.

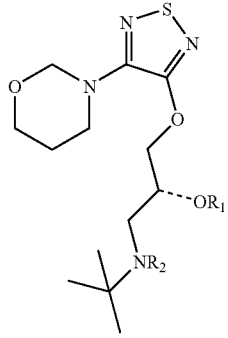

(III)

Further expected to be within the scope of the invention are analogues of metoprolol of formula (IV) wherein $R_1$ is hydrogen or lower alkyl and $R_2$ is hydrogen or lower alkyl, with the proviso that both $R_1$ and $R_2$ are not hydrogen.

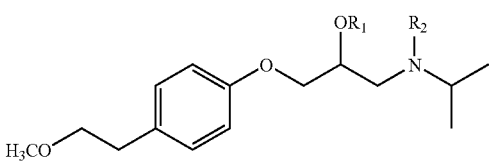

(IV)

In the case of salts, it is well known that organic compounds, including compounds having activities suitable for methods according to the present invention, have multiple groups that can accept or donate protons, depending upon the pH of the solution in which they are present. These groups include carboxyl groups, hydroxyl groups, amino groups, sulfonic acid groups, and other groups known to be involved in acid-base reactions. The recitation of a compound or analogue includes such salt forms as occur at physiological pH or at the pH of a pharmaceutical composition unless specifically excluded.

Similarly, prodrug esters can be formed by reaction of either a carboxyl or a hydroxyl group on compounds or analogues suitable for methods according to the present invention with either an acid or an alcohol to form an ester. Typically, the acid or alcohol includes a lower alkyl group such as methyl, ethyl, propyl, isopropyl, butyl, isobutyl, and tertiary butyl. These groups can be substituted with substituents such as hydroxy, or other substituents. Such prodrugs are well known in the art and need not be described further here. The prodrug is converted into the active compound by hydrolysis of the ester linkage, typically by intracellular enzymes. Other suitable groups that can be used to form prodrug esters are well known in the art. For example prodrugs can include amides prepared by reaction of the parent acid compound with a suitable amine. In some cases it is desirable to prepare double ester type prodrugs such as (acyloxy) alkyl esters or ((alkoxycarbonyl)oxy)alkyl esters. Suitable esters as prodrugs include, but are not necessarily limited to, methyl, ethyl, propyl, isopropyl, n-butyl, isobutyl, tert-butyl, morpholinoethyl, and N,N-diethylglycolamido. Methyl ester prodrugs may be prepared by reaction of the acid form of a compound having a suitable carboxylic acid group in a medium such as methanol with an acid or base esterification catalyst (e.g., NaOH, H$_2$SO$_4$). Ethyl ester prodrugs are prepared in similar fashion using ethanol in place of methanol. Morpholinylethyl ester prodrugs may be prepared by reaction of the sodium salt of a suitable compound (in a medium such as dimethylformamide) with 4-(2-chloroethyl)morphine hydrochloride (available from Aldrich Chemical Co., Milwaukee, Wis. USA.

Pharmaceutically acceptable salts include acid salts such as hydrochloride, hydrobromide, hydroiodide, sulfate, phosphate, fumarate, maleate, acetates, citrates, lactates, tartrates, sulfamates, malonate, succinate, tartrate, methanesulfonates, ethanesulfonates, benzenesulfonates, p-toluenesulfonates, cyclohexylsulfamates, quinates, formates, cinnamates, picrates, and other suitable salts. Such salts can be derived using acids such as hydrochloric acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, and quinic acid.

Pharmaceutically acceptable salts also include salts with bases such as alkali metal salts such as sodium or potassium, as well as pyridine salts, ammonium salts, piperazine salts, diethylamine salts, nicotinamide salts, calcium salts, magnesium salts, zinc salts, lithium salts, methylamino salts, triethylamino salts, dimethylamino salts, and tris(hydroxymethyl)aminomethane salts.

The subject to be treated can be a human patient or a socially or economically important animal, including, but not limited to, a dog, a cat, a horse, a sheep, a goat, or a pig. Methods according to the present invention are not limited to the treatment of humans.

Typically, the method of administration of the $\beta_2$-adrenergic inverse agonist results in continuous levels of the $\beta_2$-adrenergic inverse agonist in the bloodstream of the subject. Typically, the method exerts a therapeutic effect that is an upregulation of pulmonary $\beta_2$-adrenergic receptors. Typically, the method exerts a therapeutic effect that is increased pulmonary airway relaxation responsiveness to $\beta_2$-adrenergic agonist drugs. This provides for combination therapy, discussed in detail below.

The $\beta$-adrenergic inverse agonist can be administered in conjunction with one or more pharmaceutical excipients. The pharmaceutical excipients can include, but are not necessarily limited to, calcium carbonate, calcium phosphate, various sugars or types of starch, cellulose derivatives, gelatin, vegetable oils, polyethylene glycols and physiologically compatible solvents. Other pharmaceutical excipients are well known in the art. The $\beta$-adrenergic inverse agonist can be administered in conjunction with one or more pharmaceutically acceptable carriers. Exemplary pharmaceutically acceptable carriers include, but are not limited to, any and/or all of solvents, including aqueous and non-aqueous solvents, dispersion media, coatings, antibacterial and/or antifungal agents, isotonic and/or absorption delaying agent, and/or the like. The use of such media and/or agents for pharmaceutically active substances is well known in the art. Except insofar as any conventional medium, carrier, or agent is incompatible with the active ingredient or ingredients, its use in a composition according to the present invention is contemplated. Supplementary active ingredients can also be incorporated into the compositions, especially as described below under combination therapy. For administration of any of the compounds used in the present invention, preparations should meet sterility, pyrogenicity, general safety, and purity standards as required by the FDA Office of Biologics Standards or by other regulatory organizations regulating drugs.

Thus, the $\beta$-adrenergic inverse agonist can be formulated for oral, sustained-release oral, buccal, sublingual, inhalation, insufflation, or parenteral administration.

If the $\beta$-adrenergic inverse agonist is administered orally, either in a conventional or a sustained-release preparation, it is typically administered in a conventional unit dosage form such as a tablet, a capsule, a pill, a troche, a wafer, a powder, or a liquid such as a solution, a suspension, a tincture, or a syrup. Oral formulations typically include such normally employed excipients as, for example, pharmaceutical grades of mannitol, lactose, starch, magnesium stearate, sodium saccharin, cellulose, magnesium carbonate, and other conventional pharmaceutical excipients. In certain defined embodiments, oral pharmaceutical compositions will comprise an inert diluent and/or assimilable edible carrier, and/or they may be enclosed in hard or soft shell gelatin capsules. Alternatively, they may be compressed into tablets. As another alternative, particularly for veterinary practice, they can be incorporated directly into food. For oral therapeutic administration, they can be incorporated with excipients or used in the form of ingestible tablets, buccal tablets, dragees, pills, troches, capsules, wafers, or other conventional dosage forms.

The tablets, pills, troches, capsules, wafers, or other conventional dosage forms can also contain the following: a binder, such as gum tragacanth, acacia, cornstarch, sorbitol, mucilage of starch, polyvinylpyrrolidone, or gelatin; excipients or fillers such as dicalcium phosphate, lactose, microcrystalline cellulose, or sugar; a disintegrating agent such as potato starch, croscarmellose sodium, or sodium starch glycolate, or alginic acid; a lubricant such as magnesium stearate, stearic acid, talc, polyethylene glycol, or silica; a sweetening agent, such as sucrose, lactose, or saccharin; a wetting agent such as sodium lauryl sulfate; or a flavoring agent, such as peppermint, oil of wintergreen, orange flavoring, or cherry flavoring. When the dosage unit form is a capsule, it can contain, in addition to materials of the above types, a liquid carrier. Various other materials can be present as coatings or to otherwise modify the physical form and properties of the dosage unit. For instance, tablets, pills, or capsules can be coated with shellac, sugar, or both. The pharmaceutical compositions of the present invention may be manufactured in a manner that is itself known, e.g., by means of conventional mixing, dissolving, granulating, dragee-making, levitating, emulsifying, encapsulating, entrapping or lyophilizing processes.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

In one alternative, a sustained-release formulation is used. Sustained-release formulations are well-known in the art. For example, they can include the use of polysaccharides such as xanthan gum and locust bean gum in conjunction with carriers such as dimethylsiloxane, silicic acid, a mixture of mannans and galactans, xanthans, and micronized seaweed, as recited in U.S. Pat. No. 6,039,980 to Baichwal, incorporated herein by this reference. Other sustained-release formulations incorporate a biodegradable polymer, such as the lactic acid-glycolic acid polymer recited in U.S. Pat. No. 6,740,634 to Saikawa et al., incorporated herein by this reference. Still other sustained-release formulations incorporate an expandable lattice that includes a polymer based on polyvinyl alcohol and polyethylene glycol, as recited in U.S. Pat. No. 4,428,926 to Keith, incorporated herein by this reference. Still other sustained-release formulations are based on the Eudragit™ polymers of Rohm & Haas, that include copolymers of acrylate and methacrylates with quaternary ammonium groups as functional groups as well as ethylacrylate methylmethacrylate copolymers with a neutral ester group. A particularly-preferred extended release composition suitable for use in methods according to the present invention is an extended-release composition that contains nadolol as its active ingredient.

Oral liquid preparations can be in the form of, for example, aqueous or oily suspensions, solutions, emulsions, syrups, tinctures, or elixirs, or can be presented as a dry product for reconstitution with water or other suitable vehicles before use. Such liquid preparations can contain conventional additives such as suspending agents, for example, sorbitol syrup, methylcellulose, glucose/sugar syrup, gelatin, hydroxymethylcellulose, carboxymethylcellulose, aluminum stearate gel, or hydrogenated edible fats; emulsifying agents, such as lecithin, sorbitan monooleate, or acacia; non-aqueous vehicles (which may include edible oils), for example, almond oil, fractionated coconut oil, oily esters, propylene glycol, or ethyl alcohol; or preservatives, for example, methylparaben, propylparaben, or sorbic acid. The preparations can also contain buffer salts, flavoring, coloring, or sweetening agents (e.g., mannitol) as appropriate.

One skilled in the art recognizes that the route of administration is an important determinant of the rate of efficiency of absorption. For example, the alimentary route, e.g., oral, rectal, sublingual, or buccal, is generally considered the safest route of administration. The delivery of the drugs into the circulation is slow, thus eliminating rapid high blood levels of the drugs that could potentially have adverse acute effects. Although this is considered the safest route of administration, there are several disadvantages. One important disadvantage is that the rate of absorption varies, which is a significant problem if a small range in blood levels separates a drug's desired therapeutic effect from its toxic effect, i.e., if the drug has a relatively low therapeutic index. Also, patient compliance is not always ensured, especially if the rectal route of administration is chosen or if oral administration is perceived by the patient as unpleasant. Furthermore, with oral administration, extensive hepatic metabolism can occur before the drug reaches its target site. Another route of administration is parenteral, which bypasses the alimentary tract. One important advantage of parenteral administration is that the time for the drug to reach its target site is decreased, resulting in a rapid response, which is essential in an emergency. Furthermore, parenteral administration allows for delivery of a more accurate dose. Parenteral administration also allows for more rapid absorption of the drug, which can result in increased adverse effects. Unlike alimentary administration, parenteral administration requires a sterile formulation of the drug and aseptic techniques are essential. The most significant disadvantage to parenteral administration is that it is not suitable for insoluble substances. In addition to alimentary and parenteral administration routes, topical and inhalation administrations can be useful. Topical administration of a drug is useful for treatment of local conditions; however, there is usually little systemic absorption. Inhalation of a drug provides rapid access to the circulation and is the common route of administration for gaseous and volatile drugs, or drugs that can be vaporized or nebulized. It is also a desired route of administration when the targets for the drug are present in the pulmonary system.

When compounds are formulated for parenteral administration, e.g., formulated for injection via the intravenous, intramuscular, subcutaneous, intralesional, or intraperitoneal routes, many options are possible. The preparation of an aqueous composition that contains an effective amount of the β-adrenergic inverse agonist as an active ingredient will be known to those of skill in the art. Typically, such compositions can be prepared as injectables, either as liquid solutions and/or suspensions. Solid forms suitable for use to prepare solutions and/or suspensions upon the addition of a liquid prior to injection can also be prepared. The preparations can also be emulsified.

The pharmaceutical forms suitable for injectable use include sterile aqueous solutions and/or dispersions; formulations including sesame oil, peanut oil, synthetic fatty acid esters such as ethyl oleate, triglycerides, and/or aqueous propylene glycol; and/or sterile powders for the extemporaneous preparation of sterile injectable solutions and/or dispersions. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. In all cases the form must be sterile and/or must be fluid to the extent that the solution will pass readily through a syringe and needle of suitable diameter for administration. It must be stable under the conditions of manufacture and storage and must be preserved against the contaminating action of microorganisms, such as bacteria or fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and/or mixtures thereof and/or in oils. Under ordinary conditions of storage and use, these preparations contain a preservative to prevent the growth of microorganisms. Suitable non-sensitizing and non-allergenic preservatives are well known in the art.

The carrier can also be a solvent and/or dispersion medium containing, for example, water, ethanol, a polyol (for example, glycerol, propylene glycol, and/or liquid polyethylene glycol, and/or the like), suitable mixtures thereof, and/or vegetable oils. The proper fluidity can be maintained for example, by the use of a coating, such as lecithin, by the maintenance of a suitable particle size in the case of a dispersion, and/or by the use of surfactants. The prevention of the action of microorganisms can be brought about by the inclusion of various antibacterial and/or antifungal agents, for example, parabens, chlorobutanol, phenol, sorbic acid, or thimerosal. In many cases it will be preferable to include isotonic agents, for example, sugars or sodium chloride. In many cases, it is preferable to prepare the solution in physiologically compatible buffers such as Hanks's solution, Ringer's solution, or physiological saline buffer. Prolonged absorption of the injectable compositions can be brought about by the use in the compositions of agents delaying absorption, for example, aluminum monostearate and/or gelatin.

Sterile injectable solutions are prepared by incorporating the active compounds in the required amount in the appropriate solvent with various of the other ingredients enumerated above, as required, followed by sterilization. Sterilization is typically performed by filtration. Generally, dispersions are prepared by incorporating the various sterilized active ingredients into a sterile vehicle which contains the basic dispersion medium and/or the other required ingredients. In the case of sterile powders for the preparation of sterile injectable solutions, the preferred methods of preparation are vacuum-drying and/or freeze-drying techniques that yield a powder of the active ingredients plus any additional desires ingredients from a previously sterile-filtered solution thereof. The preparation of more-concentrated or highly-concentration solutions for direct injection is also contemplated, where the use of dimethyl sulfoxide (DMSO) as solvent is envisioned to result in extremely rapid penetration, delivering high concentrations of the active agents to a small area if desired.

For parenteral administration in an aqueous solution, for example, the solution should be suitably buffered if necessary and/or the liquid diluent first rendered isotonic with sufficient saline, glucose, or other tonicity agent. These particular aqueous solutions are especially suitable for intravenous, intramuscular, subcutaneous, or intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected into the proposed site of infusion (see, e.g., "Remington's Pharmaceutical Sciences" ($15^{th}$ ed.), pp. 1035-1038, 1570-1580). Some variation in dosage will necessarily occur depending on the condition of the subject being treated. The person responsible for administration will, in any event, determine the appropriate dose for the individual subject. Compounds and compositions according to the invention can also be formulated for parenteral administration by bolus injection or continuous infusion and can be presented in unit dose form, for instance as ampoules, vials, small volume infusions, or pre-filled syringes, or in multi-dose containers with an added preservative.

Another route of administration of compositions according to the present invention is nasally, using dosage forms such as nasal solutions, nasal sprays, aerosols, or inhalants. Nasal solutions are usually aqueous solutions designed to be administered to the nasal passages in drops or sprays. Nasal solutions are typically prepared so that they are similar in many respects to nasal secretions, so that normal ciliary action is maintained. Thus, the aqueous nasal solutions usually are isotonic and/or slightly buffered in order to maintain a pH of from about 5.5 to about 6.5. In addition, antimicrobial preservatives, similar to those used in ophthalmic preparations, and/or appropriate drug stabilizers, if required, can be included in the formulation. Various commercial nasal preparations are known and can include, for example, antibiotics or antihistamines. Spray compositions can be formulated, for example, as aqueous solutions or suspensions or as aerosols delivered from pressurized packs, with the use of a suitable propellant, such as dichlorodifluoromethane, trichlorofluoromethane, dichlorotetrafluoroethane, 1,1,1,2,3,3,3-heptafluoropropane, 1,1,1,2-tetrafluoroethane, carbon dioxide, or other suitable gas.

Additional formulations that are suitable for other modes of administration include vaginal suppositories and/or pessaries. A rectal pessary or suppository can also be used. Suppositories are solid dosage forms of various weights or shapes, usually medicated, for insertion into the rectum, vagina, or urethra. After insertion, suppositories soften, melt, and/or dissolve into the cavity fluids. In general, for suppositories, traditional binders or carriers can include polyalkylene glycols, cocoa butter, or triglycerides.

Other dosage forms, including but not limited to liposomal formulations, ointments, creams, lotions, powders, or creams, can alternatively be used. Ointments and creams can, for example, be formulated with an aqueous or oily base with the addition of suitable gelling agents and/or solvents. Such bases, can thus, for example, include water and/or an oil such as liquid paraffin or a vegetable oil such as arachis (peanut) oil or castor oil or a solvent such as a polyethylene glycol. Thickening agents which can be used include soft paraffin, aluminum stearate, cetostearyl alcohol, polyethylene glycols, microcrystalline wax, and beeswax. Lotions can be formulated with an aqueous or oily base and will in general also contain one or emulsifying agents, stabilizing agents, dispersing agents, suspending agents, or thickening agents.

Powders for external application can be formed with the aid of any suitable powder base, for example, talc, lactose, or starch.

Because of the nature of the interaction between inverse agonists and the β-adrenergic receptors with which they interact, the therapeutic response develops gradually over time as the receptor density in the affected tissues increases in response to the administration of inverse agonists. Therefore, in one particularly preferred alternative, the dosage is titrated at the start of administration with gradual increases. In other words, the β-adrenergic inverse agonist is administered over time in a series of graduated doses starting with the lowest dose and increasing to the highest dose. When the highest dose is reached, the β-adrenergic inverse agonist continues to be administered at that dose (the maintenance dose). For example, with nadolol administered orally, treatment can begin with 1 mg dosages, then progress through 3 mg, 5 mg, 10 mg, 15 mg, and then to higher maintenance dosages such as 25 mg, 30 mg, 50 mg, 70 mg, 100 mg, or higher as deemed necessary, depending on the particular condition to be treated, the severity, and the response of the condition to the treatment. Analogous dosing regimens can be used with other inverse agonists, the exact starting dose typically depending on the affinity of the inverse agonist for the binding site of the β-adrenergic receptor.

Accordingly, another aspect of the invention is a blister pack that includes a range of dosages from the lowest initial dose to the highest maintenance dose of a β-adrenergic inverse agonist such as nadolol. In general, such a blister pack comprises:

(1) a lower substrate;

(2) an intermediate dosage holder that is shaped to generate a plurality of cavities and that is placed over the lower substrate, the cavities being shaped to hold dosage forms of a β-adrenergic inverse agonist;

(3) an upper substrate placed over the intermediate dosage holder that has a plurality of apertures, each aperture being located to accommodate a corresponding cavity; wherein the dosage forms are of graduated dosages starting with a lowest dose and proceeding to a highest dose; and (4) dosage forms of a β-adrenergic inverse agonist placed in the cavities.

A suitable blister pack 10 is shown in FIG. 1 and includes a lower substrate 12 that is typically foil, an intermediate dosage holder 14 that is shaped to generate a plurality of cavities 16, 18, 20, and 22 shaped to hold the pills, capsules, or other dosage forms that is placed over the lower substrate, and an upper substrate 24 placed over the intermediate dosage holder 14 that has apertures 26, 28, 30, and 32, each aperture being located to accommodate the cavities 16, 18, 20, and 22. Only four cavities and apertures are shown here, but blister packs 10 according to the present invention can hold a larger number of dosage forms, such as 10, 20, or 30. Typically, either the lower substrate 12, the upper substrate 24, or both have printed instructions on it to identify the dosage of each pill, capsule, or other dosage forms, and to provide guidance to the patient as to the sequence to be followed in taking the pills, capsules, or other dosage forms. The intermediate dosage holder 14 is typically made of a transparent plastic or other transparent material so that the dosage forms can be viewed. The dosage forms can be of graduated doses, starting with a lowest dose and proceeding to a highest dose, which is generally the maintenance dose, as described above. Alternatively, the dosage forms can be of at least two dosages: (1) a maintenance dose that is the highest in a series of graduated doses; and (2) at least one backup restoration dose (to be used, e.g., if a dose is missed) or a lower dose to be taken in a specified condition. The specified condition can be, for example, the administration of an antibiotic, such as erythromycin or neomycin, where lower dosages are generally required or when kidney malfunction increases the half-life of the drug necessitating a lower dose to achieve the same serum concentration when kidney function was normal.

Various factors must be taken into account in setting suitable dosages for β-adrenergic inverse agonists. These factors include whether the patient is taking other medications that can alter the pharmacokinetics of the β-adrenergic inverse agonists, either causing them to be degraded more rapidly or more slowly. In particular, if the patient is taking the antibiotics erythromycin or neomycin, it is typically necessary to decrease the maintenance dose. Another aspect of the invention is therefore a blister pack that has backup restoration doses and lower doses for use when the patient is taking these antibiotics.

Toxicity and therapeutic efficacy of β-adrenergic inverse agonists can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized.

For any compound used in the method of the invention, the therapeutically effective dose can be estimated initially from cell culture assays. For example, a dose can be formulated in animal models to achieve a circulating plasma concentration range that includes the $IC_{50}$ as determined in cell culture (i.e., the concentration of the test compound which achieves a half-maximal improvement in receptor signaling when chronic effects are considered). Such information can be used to more accurately determine useful doses in humans. Levels in plasma may be measured, for example, by HPLC.

The exact formulation, route of administration and dosage can be chosen by the individual physician in view of the patient's condition. (See e.g. Fingl et al., in The Pharmacological Basis of Therapeutics, 1975, Ch. 1 p. 1). It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administered dose in the management of the disorder of interest will vary with the severity of the condition to be treated and to the route of administration. The severity of the condition may, for example, be evaluated, in part, by standard prognostic evaluation methods. Further, the dose and perhaps the dose frequency, will also vary according to the age, body weight, and response of the individual patient. A program comparable to that discussed above may be used in veterinary medicine.

Depending on the specific conditions being treated, such agents may be formulated and administered systemically or locally. Typically, administration is systemic. Techniques for formulation and administration may be found in Remington's Pharmaceutical Sciences, 18th ed., Mack Publishing Co., Easton, Pa. (1990). Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few. Typically, oral administration is preferred.

For injection, the agents of the invention may be formulated in aqueous solutions. For such transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein. In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions. The pharmaceutical compositions of the present invention may be manufactured in a manner that is itself known, e.g., by means of conventional mixing, dissolving, granulating, dragee-making, levitating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

Typically, in methods according to the present invention, the inverse agonist is administered in a daily dose or multiple times per day, depending on the half-life of the inverse agonist. Alternatively, the inverse agonist can be administered less frequently, such as every other day, every third day, every fourth day, every week, and the like. One skilled in the art of pharmacokinetics will recognize the importance of understanding the bioavailability and the half-life of a drug in relation to dosing of the particular drug. It is well known that a drug accumulates in the body if the time interval between doses is less than four of its half-lives, in which case, the total body stores of the drug are increased exponentially to a plateau or steady-state concentration. The average total body store of a drug at the plateau is a function of the dose, the interval between doses, the bioavailability of the drug, and the rate of the elimination of the drug. Thus, one of ordinary skill in the art is capable of determining the dose and interval of the dose for a given drug to achieve the desired effect.

Another embodiment of the present invention is methods and compositions that incorporate multiple-drug or combination therapy for the treatment of pulmonary airway diseases. Patients with pulmonary airway diseases often are prescribed multiple drugs that work in combination to control their symptoms.

Although Applicant does not intend to be bound by this theory, it is believed that, in many circumstances, co-treatment with an inverse agonist and with an agonist is superior to treatment with the agonist alone. These results suggest that co-treatment with the inverse agonist may increase the therapeutic efficacy of the agonist and prevent desensitization of the relevant GPCR. One rationale for this form of combination therapy may lie in the treatment of acute episodes such as acute asthma attacks. Even if treatment with inverse agonists decreases the frequency of asthma attacks, there is still a need to treat the acute attack. This can be done by co-administration of the inverse agonist and the agonist.

In one particularly desirable combination, the β-adrenergic inverse agonists are administered in combination with $β_2$-selective adrenergic agonists for the treatment of pulmonary airway diseases. The $β_2$-selective adrenergic agonists are typically selected from the group consisting of albuterol, bitolterol, clenbuterol, clorprenaline, dobutamine, fenoterol, formoterol, isoetharine, isoprenaline, levabuterol, mabuterol, metaproterenol, pirbuterol, ritodrine, salbutamol, salmeterol, and terbutaline, as well as the salts, solvates, analogues, congeners, bioisosteres, hydrolysis products, metabolites, precursors, and prodrugs thereof. A particularly preferred β-adrenergic inverse agonist according to the present invention for use in such combination therapy is nadolol. Particularly preferred $β_2$-selective adrenergic agonists for use in combination with β-adrenergic inverse agonists include isoproterenol, salbutamol, and salmeterol. The principle of combination therapy is supported by the data that shows that treatment with inverse agonists causes upregulation of the receptor number. In that case, co-treatment with an agonist would be expected to increase cellular signaling and restore normal function in those circumstances in which the pathological response is characterized by a deficiency in signaling. Along these lines, the inhibitory response of inverse agonists on airway resistance would be increased in magnitude by the co-administration of agonists. The potency of these agonists may be reduced due to the presence of the inverse agonist, but the overall magnitude of the response would be increased. This would prevent the desensitization often associated with chronic agonist treatment.

When combination therapy is used, the dosages of each member of the combination can be determined according to the principles described above. However, in many cases, fixed dose combinations are desirable and can be used. In the fixed dose combinations, the dosage of the β-adrenergic inverse agonists are as described above, while the desirable dosage of the $β_2$-selective adrenergic agonist can be determined as described above.

In another desirable combination, β-adrenergic inverse agonists are administered together with steroids. The steroids especially preferred for use according to the invention include, but are not necessarily limited to, beclomethasone, budenoside, ciclesonide, flunisolide, fluticasone, methylprednisolone, prednisolone, prednisone, and triamcinolone, as well as the salts, solvates, analogues, congeners, bioisosteres, hydrolysis products, metabolites, precursors, and prodrugs thereof.

In another desirable combination, β-adrenergic inverse agonists are administered together with anticholinergics. The anticholinergics especially preferred for use according to the invention include, but are not necessarily limited to, muscarinic receptor antagonists, especially quaternary ammonium muscarinic receptor antagonists such as ipratropium bromide, tiotropium bromide, and oxitropium bromide, as well as the salts, solvates, analogues, congeners, bioisosteres, hydrolysis products, metabolites, precursors, and prodrugs thereof.

In yet another desirable combination, β-adrenergic inverse agonists are administered together with a xanthine compound. Xanthine compounds especially preferred for use according to the invention include, but are not necessarily limited to, theophylline, extended-release theophylline, aminophylline, theobromine, enprofylline, diprophylline, isbufylline, choline theophyllinate, albifylline, arofylline, bamifylline and caffeine, as well as the salts, solvates, analogues, congeners, bioisosteres, hydrolysis products, metabolites, precursors, and prodrugs thereof.

In yet another desirable combination, β-adrenergic inverse agonists are administered together with an anti-IgE antibody. Typically, the anti-IgE antibody is a monoclonal antibody or a genetically engineered antibody that is derived from a monoclonal antibody. Preferably, the anti-IgE antibody is humanized. A particularly preferred humanized anti-IgE antibody is an IgG1 κ monoclonal antibody that specifically binds to human IgE and is marketed under the name of omalizumab.

In still another desirable combination, β-adrenergic inverse agonists are administered together with a leukotriene modifier. The leukotriene modifiers especially preferred for use according to the present invention include, but are not necessarily limited to, ibudilast, montelukast, pranlukast, and zafirlukast, as well as the salts, solvates, analogues, congeners, bioisosteres, hydrolysis products, metabolites, precursors, and prodrugs thereof.

In still another desirable combination, β-adrenergic inverse agonists are administered together with a phosphodiesterase IV inhibitor. The phosphodiesterase IV inhibitors especially preferred according to the present invention include, but are not necessarily limited to, roflumilast and cilomilast, as well as the salts, solvates, analogues, congeners, bioisosteres, hydrolysis products, metabolites, precursors, and prodrugs thereof. Phosphodiesterase IV is the predominant isoform in the lung and inhibitors of this enzyme are being considered for the treatment of asthma and COPD.

The route of administration of the β-adrenergic inverse agonist and of the additional therapeutic agent can be chosen by one of ordinary skill in the art to optimize therapeutic efficiency, as described above. However, in one preferred alternative, both the β-adrenergic inverse agonist and the additional therapeutic agent are administered by inhalation. In another preferred alternative, the β-adrenergic inverse agonist is administered orally, while the additional therapeutic agent is administered by inhalation. The administration of the additional therapeutic agent by inhalation is typically preferred because of possible toxicity of some of these additional therapeutic agents. However, other routes are possible.

Aerosol therapy allows an almost ideal benefit to risk ratio to be achieved because very small doses of inhaled medication provide optimal therapy with minimal adverse effects. A variety of additional therapeutic agents suitable for use in methods according to the present invention are available in aerosol formulation, including $β_2$-adrenergic agonists, steroids, and anticholinergics. However, the therapeutic efficiency of drugs administered by aerosolization depends not only on the pharmacological properties of the drugs themselves, but also on the characteristics of the delivery device. The characteristics of the delivery device influence the amount of drug deposited in the lungs and the pattern of drug distribution in the airways.

Aerosols are airborne suspensions of fine particles. The particles may be solids or liquids. Aerosol particles are heterodisperse (i.e. the particles are of a range of sizes) and aerosol particle size distribution is best described by a log normal distribution. Particles tend to settle (sediment), adhere to each other (coagulate), and adhere to structures such as tubing and mucosa (deposit). The particles delivered by aerosol can be conveniently characterized on the basis of their aerodynamic behavior. One parameter is the mass median aerodynamic diameter (MMAD). By definition, a particle distribution with an MMAD of 1 μM has the same average rate of settling as a droplet of unit density and 1 μM diameter.

The size of an aerosol particle, as well as variables affecting the respiratory system, influence the deposition of inhaled aerosols in the airways. On one hand, particles larger than 10 μM in diameter are unlikely to deposit in the lungs. However, particles smaller than 0.5 μM are likely to reach the alveoli or may be exhaled. Therefore, particles that have a diameter of between 1 μM and 5 μM are most efficiently deposited in the lower respiratory tract. Particles of these sizes are most efficient for the delivery of therapeutic agents for asthma.

The percentage of the aerosol mass contained within respirable droplets (i.e., droplets with a diameter smaller than 5 μM), depends on the inhalation device being used. Slow, steady inhalation increases the number of particles that penetrate the peripheral parts of the lungs. As the inhaled volume is increased, the aerosol can penetrate more peripherally into the bronchial tree. A period of breath-holding, on completion of inhalation, enables those particles that have penetrated to the lung periphery to settle into the airways via gravity. Increased inspiratory flow rates, typically observed in patients with acute asthma, result in increased losses of inhaled drug. This occurs because aerosol particles impact in the upper airway and at the bifurcations of the first few bronchial divisions. Other factors associated with pulmonary airway disease may also alter aerosol deposition. Airway obstruction and changes in the pulmonary parenchyma are often associated with pulmonary deposition in the peripheral airways in patients with asthma.

In aerosol administration, the nose efficiently traps particles before their deposition in the lung; therefore, mouth breathing of the aerosolized particles is preferred. The aerosolized particles are lost from many sites. Generally, the amount of the nebulized dose reaching the small airways is ≤15%. In many cases, approximately 90% of the inhaled dose is swallowed and then absorbed from the gastrointestinal tract. The small fraction of the dose that reaches the airways is also absorbed into the blood stream. The swallowed fraction of the dose is, therefore, absorbed and metabolized in the same way as an oral formulation, while the fraction of the dose that reaches the airways is absorbed into the blood stream and metabolized in the same way as an intravenous dose.

When drugs are administered topically (via aerosol delivery to the lungs), the desired therapeutic effects depend on local tissue concentrations, which may not be directly related to plasma drug concentrations. If a sufficiently large dosage of any drug is given, systemic activity can easily be demonstrated with any inhaled $\beta_2$-agonists or corticosteroid. This has several implications. First, for the selection of a drug to be inhaled, topical drugs must combine a high intrinsic activity within the target organ and rapid inactivation of the systemically absorbed drug. Secondly, fewer systemic adverse effects should be expected with drugs that have a low oral bioavailability (whether due to poor gastrointestinal absorption or high first-pass hepatic metabolism). Because most inhaled drugs are administered at a low dosage and have a low oral bioavailability, plasma concentrations of these drugs are much lower than after oral administration.

Furthermore, factors influencing pulmonary absorption should be considered. It was recently demonstrated that terbutaline was absorbed through the lung more rapidly in healthy smokers than in healthy nonsmokers. This may affect the onset of action of the drug. It has also been found that the bioavailability of inhaled salbutamol in 10 patients with cystic fibrosis was greater than that in healthy adults. One proposed mechanism for this difference in bioavailability is that the chronically diseased tracheobronchial tree in patients with cystic fibrosis results in higher permeability of salbutamol in this tissue. However, data are limited in this area, and further investigation is required to substantiate these claims.

Finally, the absolute pulmonary bioavailability of inhaled drugs is difficult to assess because blood concentrations are low, and pulmonary and oral absorption should be discriminated for pulmonary bioavailability to be determined as accurately as possible. Charcoal can be used to adsorb the swallowed fraction of inhaled terbutaline to discriminate the pulmonary absorption of the drug. Recently, it was shown that a urine collection during the 30 minutes after inhalation of salbutamol represents the amount of drug delivered to the lungs. This technique may be applicable for the determination of bioavailability of other inhaled drugs. Other techniques for the determination of bioavailability of inhaled drugs are also known in the art; these include pharmacodynamic methods using $FEV_1$ measurements, lung deposition studies using radiolabeled formulations, or pharmacokinetic studies using predominantly urinary excretion measurements.

Therapeutic aerosols are commonly produced by atomization of liquids within jet nebulizers or by vibration of a standing pool of liquid (ultrasonic nebulisation). Preformed aerosols may also be administered. Examples of the latter include MDIs and dry powder devices. Whatever delivery device is used, patients should be taught to use it correctly.

All jet nebulizers work via a similar operating principle, represented by the familiar perfume atomizer. A liquid is placed at the bottom of a closed container, and the aerosol is generated by a jet of air from either a compressor or a compressed gas cylinder passing through the device. Ultrasonic nebulizers produce an aerosol by vibrating liquid lying above a transducer at frequencies of about 1 mHz. This produces a cloud of particles that is carried out of the device to the patient by a stream of air. Aerosols varying in quantity, size and distribution of panicles can be produced by nebulizers, depending upon the design of the nebulizers and how it is operated. It should be noted that not all nebulizers have the required specifications (MMAD, flow, output) to provide optimum efficacy. A recent study compared the lung deposition from 4 nebulizers in healthy volunteers and showed that median lung aerosol deposition, expressed as percentages of the doses initially loaded into the nebulizers, ranged from 2 to 19%. Nebulized aerosols are particularly useful for children under 5 years of age and in the treatment of severe asthma where respiratory insufficiency may impair inhalation from an MDI or dry powder inhaler. To minimize adverse effects, pH and osmolarity of the nebulized solution should be controlled.

Metered dose inhalers (MDIs), because of their convenience and effectiveness, are probably the most widely used therapeutic aerosol used for inhaled drug delivery to outpatients. Most MDIs in current use contain suspensions of drug in propellant. There are 2 major components of an MDI: (i) the canister, a closed plastic or metal cylinder that contains propellant, active medication, and the metering chamber; and (ii) the actuator, a molded plastic container that holds the canister and directs the released aerosol towards the patient's airway.

Propellant mixtures are selected to achieve the vapor pressure and spray characteristics desired for optimal drug delivery. Chlorofluorocarbons were previously used, but non-chlorinated propellants are now employed because of environmental concerns. Finely divided particles of drug, usually less than 1 µM, are suspended in the pressurized (liquefied) propellant. To prevent the drug from coagulating, a surface active agent such as sorbitan oleate, lecithin or oleic acid is typically added; other surface active agents are known in the art. Metering chambers ordinarily contain 25 to 100 µL. The contents of the metering chamber are released when the canister is depressed into the actuator. Almost instantaneously, the propellants begin to evaporate, producing disintegration of the discharged liquid into particles that are propelled forward with great momentum. For optimal pulmonary drug deposition, the medication should be released at the beginning of a slow inspiration that lasts about 5 seconds and is followed by 10 seconds of breathholding. Several inhalation aids have been designed to improve the effectiveness of a MDI. These are most useful in patients who have poor hand-to-breath coordination. A short tube (e.g. cones or spheres) may direct the aerosol straight into the mouth or collapsible bags may act as an aerosol reservoir holding particles in suspension for 3 to 5 seconds, during which time the patient can inhale the drug. However, when any of these devices is used, aerosol velocity upon entering the oropharynx is decreased and drug availability to the lungs and deposition in the oropharynx is decreased.

Dry powder inhalers have been devised to deliver agents to patients who have difficulty using an MDI (e.g. children and elderly patients). In general, the appropriate dosage is placed in a capsule along with a flow aid or filler such as large lactose or glucose panicles. Inside the device, the capsule is initially either pierced by needles (e.g. Spinhaler®) or sheared in half (e.g. Rotohaler®). During inhalation the capsule rotates or a propeller is turned, creating conditions that cause the contents of the capsule to enter the inspired air and be broken up to small particles suitable for delivery to the airways. The energy required to disperse the powder is derived from the patient's inspiratory effort. Recently, more convenient multidose dry powder inhalers have been introduced (e.g. Diskhaler®, Turbuhaler®)). Potential problems associated with dry powder inhalers include esophageal irritation and, consequently, cough due to the direct effect of powder in airways. Furthermore, the walls of the capsule may be coated with drug as a result of either failure of the capsule to release the drug or failure of the aggregated powder to break up. This may cause virtually all of the drug to be deposited in the mouth. These powder devices do not contain chlorofluorocarbons and may provide an alternative to MDIs.

The clinical use of aerosols for asthma treatment has been proposed for several compounds proposed herein as additional therapeutic agents, including $\beta_2$-agonists and corticosteroids.

For $\beta_2$-agonists, limited pharmacokinetic data are available in humans mostly because the low dosages of inhaled drugs required for therapeutic activity produce drug concentrations in body fluids that are below assay limits. Little is known about pulmonary bioavailability of those drugs. It is generally argued that an average of 10% of an inhaled dose reaches the lung when given by a MDI. The mean pulmonary bioavailability of terbutaline from an MDI was reported to be 9.1%. When the oral component (swallowed fraction of the dose) was added, the value rose to 16.5%, i.e. an increase of 6.7%. The drugs salmeterol and formoterol have different mechanisms of action underlying their prolonged duration of bronchodilatory effect (12 to 18 hours). Salmeterol appears unique because it has a long side-chain that anchors the $\beta_2$-agonist molecule to the receptor. Formoterol appears to be an extremely potent classical $\beta_2$-agonist. The elimination half-life of formoterol after inhalation was calculated to be between 1.7 and 2.3 hours on the basis of urinary excretion data. A glucuronic acid conjugate was identified. However, it is possible that formoterol has a prolonged elimination half-life that is yet to be detected in humans. Salmeterol is formulated as the xinafoate (hydroxynaphthoic acid) salt. Little is known about the pharmacokinetic properties of this drug Salmeterol is extensively metabolized by hydroxylation, with the majority of a dose being eliminated predominantly in the feces within 72 hours. The hydroxynaphthoic acid part of the molecule accumulates in plasma during repeated administration as a consequence of its long elimination half-life (12 to 15 days).

For anticholinergic agents, the parent compound of this class is atropine. Synthetic agonists of the muscarinic receptors of acetylcholine are quaternary ammonium compounds and, therefore, cross membrane barriers with difficulty. Because systemic absorption of atropine after inhalation of the drug is nearly complete, this route of administration can produce significant systemic toxicity (Harrison et al. 1986). Ipratropium bromide is the only well studied representative of this class. Absorption through the gastrointestinal tract is slow, as peak plasma concentrations have been recorded 3 hours after oral intake of the drug. The absolute bioavailability after oral intake is only 30%. Elimination of metabolized drug occurs in the urine and bile. Whatever the route of administration, the mean elimination half-life is about 3.5 hours. Plasma concentrations observed with inhaled ipratropium were a thousand times lower than those observed with an equipotent bronchodilatory dose administered orally. This explains why systemic anticholinergic effects do not occur following inhalation of therapeutic doses of ipratropium bromide. These properties are probably shared by other quaternary ammonium anticholinergic agents such as oxitropium bromide, an alternative as described above.

Corticosteroids are frequently administered by inhalation, which can prevent some of the adverse effects usually associated with systemic corticosteroid therapy. To produce a compound with marked topical activity, some of the hydroxyl groups in the hydrocortisone molecule were substituted with acetonide or ester groups. Topically active corticosteroid drugs used for the treatment of patients with asthma include beclomethasone, betamethasone valerate, budesonide, triamcinolone, fluticasone and flunisolide. Of these, beclomethasone and budesonide are the most extensively used. The results of numerous clinical studies have shown that there is little difference between the efficacy of beclomethasone and budesonide. Oropharynx deposition is reduced by using a spacing device, and the development of candidiasis can be prevented by mouth rinsing. Plasma clearance of budesonide was calculated to be 84±27 L/h, which is about 10-fold higher than the average clearance of prednisolone. As a consequence of this high clearance, the elimination half-life of budesonide is short (2.8±1.1 hours). The systemic availability of the swallowed fraction is 10.7±4.3%, indicating that there is extensive first-pass metabolism. Stereoselective metabolism was demonstrated and plasma clearance of the 2 enantiomers, when calculated on a per kilogram of bodyweight basis, were about 50% higher in 6 children with asthma than in 11 healthy adults. Therefore, administration of budesonide by inhalation should reduce the risk of systemic adverse effects compared with administration of the drug orally. Lung esterases are known to hydrolyze beclomethasone. The absorbed beclomethasone and esterase-hydrolysis products (beclomethasone 17-propionate and beclomethasone) are rapidly converted to less active metabolites during passage through the liver. First-pass hepatic metabolism of the systemically absorbed fluticasone is almost complete, and therefore the inhaled drug has a favorable pharmacokinetic profile. Few data have been published regarding the pharmacokinetic properties of flunisolide, triamcinolone and betamethasone valerate.

To ensure maximal effects from inhaled drugs, both the pharmacological characteristics of the drugs and the device used to aerosolize the drugs should be considered. With respect to $\beta_2$-agonists, different formulations, with different pulmonary disposition techniques, are available, such as for MDI administration, for administration with a dry powder inhaler, or a solution for nebulisation. A unit dose from a dry powder inhaler is twice that release from an MDI, but they have equivalent bronchodilatory effects. The characteristics of the devices vary. For a metered-dose inhaler, typically 12-40% of the dose is deposited in the lung, but up to 80% in the oropharynx. When an MDI is used with a spacer, typically about 20% of the dose is deposited in the lung, but only up to 5% in the oropharynx; thus, the use of a spacer can reduce the proportion of the drug that is deposited in the oropharynx. For a dry powder inhaler, typically 11-16% of the dose is deposited in the lung and 31-72% in the oropharynx. For a nebulizer, typically 7-32% of the dose is deposited in the lung and 1-9% is deposited in the oropharynx. One of ordinary skill in the art can ensure that the proper inhalation therapy device is used and can prepare suitable instructions. Considerations for the use of inhalation therapy are described in A.-M. Tabaret & B. Schmit, "Pharmacokinetic Optimisation of Asthma Treatment," *Clin. Pharmacokinet.* 26: 396418 (1994), incorporated herein by this reference.

For all of these combinations, the invention further encompasses blister packs that contain either a fixed-dose combination of the β-adrenergic inverse agonist and the additional therapeutic agent, such as the $\beta_2$-selective adrenergic agonist, the steroid, the anticholinergic agent, the xanthine compound, the anti-IgE antibody, the leukotriene modifier, or the phosphodiesterase-4 inhibitor, or, in separate pills, capsules, or other dosage forms, the β-adrenergic inverse agonist and the additional therapeutic agent. The use of these blister packs is appropriate when oral administration of the inverse agonist and additional therapeutic agent is desired. The blister packs follow the general design described above and in FIG. 1, and include appropriate instructions to the patient.

In general, when a fixed-dose combination is used, the blister pack comprises:

(1) a lower substrate;

(2) an intermediate dosage holder that is shaped to generate a plurality of cavities and that is placed over the lower substrate, the cavities being shaped to hold dosage forms of the pharmaceutical composition described above containing a β-adrenergic inverse agonist and an additional therapeutic agent;

(3) an upper substrate placed over the intermediate dosage holder that has a plurality of apertures, each aperture being located to accommodate a corresponding cavity; and (4) dosage forms of the pharmaceutical composition placed in the cavities.

When the β-adrenergic inverse agonist and the additional therapeutic agent are to be administered in separate dosage forms, the blister pack, in general, comprises:

(1) a lower substrate;

(2) an intermediate dosage holder that is shaped to generate a plurality of cavities and that is placed over the lower substrate, the cavities being shaped to hold dosage forms of: (a) a first pharmaceutical composition that comprises: (i) a therapeutically effective amount of a β-adrenergic inverse agonist; and (ii) a first pharmaceutically acceptable carrier; and (b) a second pharmaceutical composition that comprises: (i) a therapeutically effective amount of a second therapeutic agent effective to treat a pulmonary airway disease, the second therapeutic agent being selected from the group consisting of a $\beta_2$-selective adrenergic agonist, a steroid, an anticholinergic drug, a xanthine compound, an anti-IgE antibody, a leukotriene modifier, and a phosphodiesterase IV inhibitor; and (ii) a second pharmaceutically acceptable carrier;

(3) an upper substrate placed over the intermediate dosage holder that has a plurality of apertures, each aperture being located to accommodate a corresponding cavity; and (4) dosage forms of the first and second pharmaceutical compositions placed in the cavities.

The dosage forms of the first and second pharmaceutical compositions are as described above. Typically, in this arrangement, the dosage forms of the first pharmaceutical composition include dosages starting at a low dose and including a range of dosages up to the highest, maintenance, dose. Other dosage form arrangements are possible.

Other arrangements are possible for the blister packs.

The invention is illustrated by the following Examples. These Examples are included for illustrative purposes only, and are not intended to limit the invention.

EXAMPLES

Example 1

Airway Resistance Reduction by Chronic Administration of β-Adrenergic Inverse Agonists Methods Balb/cJ mice aged 6 weeks (Jackson Animal Laboratory, Bar Harbor, Me.) were housed under specific pathogen-free conditions and fed a chicken ovalbumin-free diet. The Animal Research Ethics Boards of both the University of Houston and the Baylor College of Medicine approved all experiments reported here. The effects of administration of the non-selective β-adrenergic inverse agonists carvedilol (GlaxoSmithKline, King of Prussia, Pa.) and nadolol (Sigma Chemical, St. Louis, Mo.) and of salbutamol (Sigma Chemical, St. Louis, Mo.), a $\beta_2$-adrenergic partial agonist, were examined in a murine model that exhibited cardinal features of human asthma, such as pulmonary eosinophilic inflammation, airway hyperresponsiveness, and heterogeneous airway narrowing. The results obtained in drug-treated animals were compared with those obtained in vehicle-treated counterparts (controls) in experiments performed in close temporal relationship. The outcome measures of the study of Example 1 included statistically-significant differences between drug-treated mice and non-treated animals in terms of baseline airway resistance, degree of airway responsiveness to cholinergic stimulation, and bronchoalveolar lavage (BALF) cellularity. Mice were sensitized with subcutaneous injection of 25 μg of ovalbumin adsorbed to aluminum hydroxide on protocol days 2, 9, and 16. Subsequently, mice were given 50 μL of saline solution containing 25 μg of ovalbumin intranasally, on a daily basis, from protocol days 23 through 27. A group of ovalbumin-sensitized saline-challenged mice serves as controls for systemic sensitization and respiratory challenges with ovalbumin. Prior to intranasal administrations, mice were sedated with halothane vapor. For the study of Example 1, ovalbumin-sensitized and ovalbumin-challenged mice, and ovalbumin-sensitized and saline-challenged mice will be referred to as asthmatic mice and control mice, respectively. The drugs used were salbutamol (a $\beta_1/\beta_2$-adrenergic agonist), alprenolol (a $\beta_1/\beta_2$-adrenergic antagonist with partial agonist activity), and nadolol and carvedilol (both non-selective $\beta_1/\beta_2$ adrenergic inverse agonists).

To examine the effects of duration of β-adrenergic ligand therapy on the phenotype of the murine model of asthma, the experimental drugs were administered either acutely or chronically to different groups of asthmatic mice.

Asthmatic mice on acute therapy were given a single intravenous bolus infusion of either β-adrenergic drug or normal saline on protocol day 28, 15 minutes before airway responsiveness to methacholine was determined. The doses of carvedilol, nadolol, alprenolol, and salbutamol administered to the mice were 24 mg/kg, 72 mg/kg, 72 mg/kg, and 0.15 mg/kg, respectively. Asthmatic mice on chronic therapy were treated with the β-adrenergic drug during protocol days 1 to 28. Those on β-antagonists had free access to chow treated with carvedilol, nadolol, or alprenolol at concentrations of 2400 ppm, 250 ppm, or 7200 ppm, respectively. These concentrations were chosen based on those producing therapeutic effects in mice in previously published studies. The non-asthmatic mice were fed normal chow. Salbutamol was delivered for 28 days at a dose of 0.5 mg/kg/day using an osmotic minipump (Alzet®, #2004, Durect Corporation, Cupertino, Calif.).

On protocol day 28, mice were anesthetized, tracheotomized, and connected to a computer-controlled small animal ventilator (Flexivent, Scientific Respiratory Equipment, Inc., Montreal, Canada). Airway resistance ($R_{aw}$) was measured using the forced oscillation technique. The cellular composition of bronchoalveolar lavage fluid (BALF) was also determined. In non-treated asthmatic mice, the degree of airway responsiveness and the number of eosinophils recovered in BALF were significantly higher compared to the ovalbumin-sensitized saline-challenged (control) mice. However, it was observed that the degree of airway responsiveness and the number of eosinophils recovered in BALF were lower in non-treated asthmatic mice studied in close temporal relationship with mice receiving acute β-adrenergic antagonist treatments that in those obtained in non-treated asthmatic mice studied concomitantly with mice on chronic β-adrenergic antagonist therapy.

To induce airway constriction, a solution containing 150 µg/mL of acetyl-α-methylcholine chloride (methacholine) (Sigma Chemical, St. Louis, Mo.) was infused intravenously at constant rates using a syringe infusion pump (Raze Scientific Instruments, Stanford, Conn.). The methacholine infusion was started at 0.008 mL/min, and its rate was doubled stepwise up to a maximum of 0.136 mL/min. Each methacholine dose was administered for 3 to 5 minutes, during which data were sampled at 1-minute intervals and then averaged.

Data Analysis

The complex input impedance of the respiratory system was computed and the value of the real part of respiratory system impedance at 19.75 Hz was taken to reflect the magnitude of airway resistance ($R_{aw}$). To examine the degree of airway responsiveness of each animal, the values for $R_{aw}$ as a function of methacholine doses were plotted. The largest value for $R_{aw}$ achieved in response to methacholine stimulation was referred to as $R_{awpeak}$. For mice that achieved a plateau in the methacholine dose-$R_{aw}$ response curve, the $ED_{50}$ was calculated by linear interpolation using the GraphPad Prism4 (GraphPad Software, Inc.). Results obtained for β-adrenergic drug treated and non-treated mice were performed using the analysis of variance for multiple groups of a Student's t-test for comparing two groups. The Bonferroni test was used to examine the statistical differences between experimental groups. The effects of acute drug treatments on baseline respiratory system mechanics were assessed using a two-tailed paired t-test. A value of $P<0.05$ was considered significant.

FIG. 2

Figure 2:
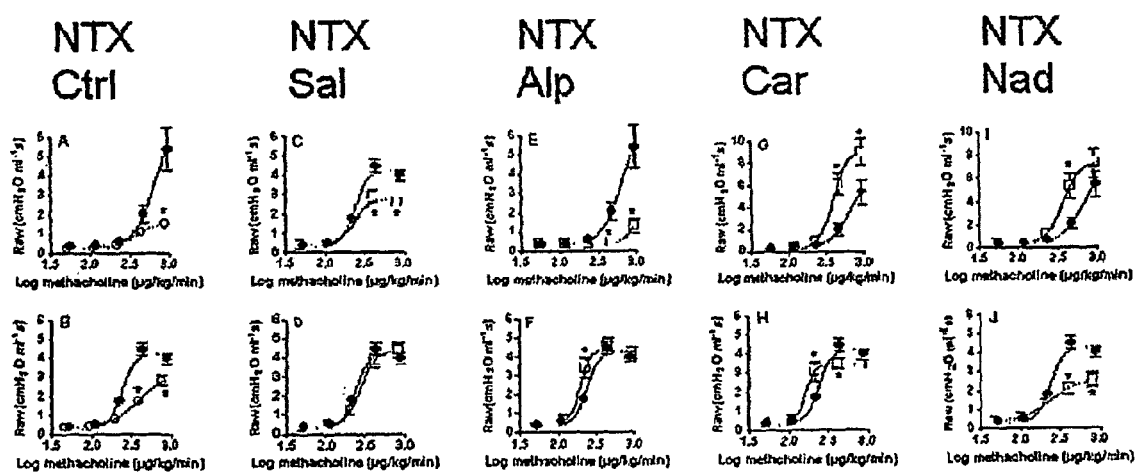
FIG. 2A is a graph showing that methacholine provocation significantly enhances airway resistance ($R_{aw}$) in asthmatic mice.
FIG. 2B is a similar graph showing that saline provocation, as a control, does not significantly enhance airway resistance in asthmatic mice.
FIG. 2C is a similar graph showing that the administration of a single intravenous bolus of salbutamol to asthmatic mice reduced the level of airway responsiveness to methacholine provocation and the level of airway resistance.
FIG. 2D is a similar graph showing that no protection was observed when salbutamol was delivered to the mice for 28 days before methacholine provocation.
FIG. 2E is a similar graph showing that when asthmatic mice were given a single intravenous bolus of alprenolol, a β-adrenergic antagonist with partial agonist activity, their airway responsiveness was diminished.
FIG. 2F is a similar graph showing that when asthmatic mice were exposed to alprenolol for 28 days, their average methacholine dose-response relationship was similar to that obtained in nontreated mice, demonstrating that this drug provides no benefit upon chronic administration.
FIG. 2G is a similar graph showing that a single intravenous bolus of carvedilol enhanced the airway responsiveness in the asthmatic mice.
FIG. 2H is a similar graph showing that chronic administration of carvedilol reduced the responsiveness of asthmatic mice to methacholine provocation.
FIG. 2I is a similar graph showing that a single intravenous bolus of nadolol also enhanced the airway responsiveness of asthmatic mice similar to that observed for carvedilol.
FIG. 2J is a similar graph showing that chronic administration of nadolol reduced the responsiveness of asthmatic mice to methacholine provocation, again, similar to that observed for carvedilol.

FIGS. 2A and 2B show that methacholine provocation significantly enhances airway resistance ($R_{aw}$) in asthmatic mice in contrast to a minimal response upon saline provocation of asthmatic mice. This demonstrates that the mouse model in this study exhibits airway hyperresponsiveness, a key feature of airway dysfunction in human asthma.

In FIG. 2C, the administration of a single intravenous bolus of salbutamol to asthmatic mice reduced the level of airway responsiveness to methacholine provocation and the level of airway resistance as expected, thus demonstrating an acute effect of this agent. However, in FIG. 2D, when salbutamol was delivered for 28 days to the mice, no protection was observed. This lack of reduction of airway hyperresponsiveness upon chronic administration of a β-adrenergic agonist has been observed in humans when tolerance to these drugs develop.

In FIG. 2E, when asthmatic mice were given a single intravenous bolus of alprenolol, a β-adrenergic antagonist with partial agonist activity, their airway responsiveness was diminished, as indicated by significant decreases in both the values for $R_{aw}$ at methacholine doses ≥408 µg/kg/min ($P<0.05$) compared with those obtained in non-treated counterparts. The reduction in airway responsiveness upon acute administration of alprenolol is similar to that observed for salbutamol, consistent with the partial agonist activity that alprenolol possesses. In FIG. 2F, when asthmatic mice were exposed to alprenolol for 28 days, their average methacholine dose-response relationship was similar to that obtained in nontreated mice, demonstrating that this drug provides no benefit upon chronic administration, as is the case with salbutamol. This is again directly analogous to the tolerance seen in human patients after long-term administration of such drugs.

In FIG. 2G, a single intravenous bolus of carvedilol enhanced the airway responsiveness in the asthmatic mice. This is consistent with previous observations in humans that acute delivery of β-adrenergic antagonists to asthmatics can result in severe airway constriction. In contrast, in FIG. 2H, chronic administration of carvedilol reduced the responsiveness of asthmatic mice to methacholine provocation.

In FIG. 2I, a single intravenous bolus of nadolol also enhanced the airway responsiveness of asthmatic mice similar to that observed for carvedilol. Chronic delivery of nadolol, as shown in FIG. 2J, also produced a decrease in airway responsiveness, which was more pronounced than that caused by carvedilol treatment. Indeed, the average methacholine dose-$R_{aw}$ response relationship obtained in asthmatic mice on chronic nadolol treatment was similar to that obtained in mice on acute salbutamol treatment.

FIG. 3

Figure 3:
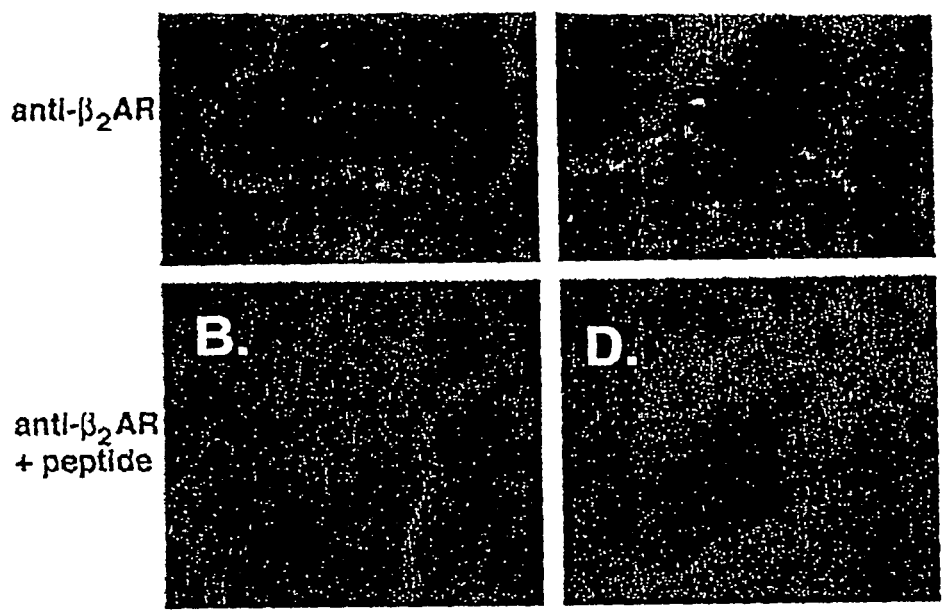
FIG. 3 is a graph showing the effects of administration of β-adrenergic receptor ligands on the peak airway responsiveness to cholinergic stimulation ((A), after treatments with the β-adrenergic agonist salbutamol; (B), after acute treatments with β-adrenergic receptor inverse agonists; and (C) after chronic treatment with β-adrenergic receptor inverse agonists.

FIG. 3 shows the effects of administration of β-adrenergic receptor ligands on the peak airway responsiveness to cholinergic stimulation in asthmatic mice. Peak $R_{aw}$ was determined for each mouse by examining the individual methacholine dose-response curves and choosing the highest $R_{aw}$ value produced by any of the methacholine doses (most often the next to last dose, 408 µg kg$^{-1}$ min$^{-1}$). Shown are the mean peak $R_{aw}$±SEM after treatments with the β-adrenergic receptor agonist salbutamol (A), after acute treatments with various agents (B) (ALP=alprenolol; CAR=carvedilol; NAD; nadolol); and after chronic treatments with the same agents used in (B), all in comparison to nontreated asthmatic mice (NTX) (black bars, n=7-25) and control mice (Ctrl, white bars, n=6-21). Values are mean±SEM for the peak $R_{aw}$ values to methacholine of n=8-19 mice. Note the change in scale of the y-axis for (B). *, $P<0.05$ compared to NTX; #, $P<0.05$ compared to Ctrl (ANOVA).

Example 2

Chronic Inverse Agonist Treatment Increases β-Adrenergic Receptor Numbers as Measured by Radioligand Binding $β_2$-adrenergic receptor numbers were measured in asthmatic mice as follows. Asthmatic mice (ovalbumin-challenged) were treated as follows: Ctrl, no drug treatment with methacholine challenge; salbutamol, a short-acting $β_2$ agonist; carvedilol, a $β_1$, $β_2$ non-selective inverse agonist with $α_1$-adrenergic antagonist activity; nadolol, a highly specific, hydrophilic $β_1$, $β_2$ non-selective inverse agonist; and alprenolol, a β-adrenergic antagonist. Drug treatments were either a single treatment 15 minutes prior to methacholine challenge or ongoing for 28 days (salbutamol was delivered continuously via a subcutaneous osmotic minipump and alprenolol, carvedilol, and nadolol were in animal chow).

Mice were sacrificed and lung membranes were isolated as follows. Frozen lung tissue was homogenized in an ice-cold buffer containing 0.32 M sucrose and 25 mM Tris (pH 7.4) using a polytron (Pro 200, Pro Scientific, Inc.). The homogenate was centrifuged at 1000×g for 10 min at 4° C. The resulting supernatant was centrifuged at 40,000×g for 20 min at 4° C. The pellet was suspended in an ice-cold 25 mM Tris-HCl buffer (pH 7.4) and centrifuged at 40,000×g for 20 min at 4° C. The final pellet was suspended in 200 µL of 25 mM Tris-HCl (pH 7.4); membrane protein concentration was determined by BCA protein assay kit. Radioligand receptor binding incubation mixtures contained membranes (~10 µg of protein), (−)3-[$^{125}$I]-cyanopindolol (ICYP) in 25 mM Tris-HCl, pH 7.4, in increasing concentrations (57500 µM) and binding buffer in a final volume of 250 µL. Propranolol was used to determine nonspecific binding. The incubation was done at 37° C. for 2 h and terminated by rapid vacuum filtration through glass fiber filters. The filters were washed three times with 250 µL of cold wash buffer (25 mM Tris-HCl, pH 7.4) and the radioactivity determined in a counter. All experiments were performed in triplicate and values are mean±SEM of n=3-5 animals in each group. Receptor densities are expressed as femtomoles of sites per milligram of protein. $B_{max}$ is determined by nonlinear regression of the saturation binding curves. Apparent $K_D$ values (in parentheses) are expressed as pM. Please note the 15 min and 28 day tome points refer to duration of drug treatment. All mice were killed at the same age and thus for vehicle treated groups (Ctrl and NTX) the groups were identical and the results pooled. #P<0.05 compared to Ctrl; *P<0.05 compared to NTX (Student's t-test).

Radioligand binding revealed that $\beta_2$-adrenergic receptor levels appear to be somewhat lower in methacholine-challenged but otherwise untreated asthmatic mice as compared with untreated, unchallenged mice, as shown in Table 1. Chronic alprenolol treatment led to a slight decrease of the level of the $\beta_2$-adrenergic receptor. The same was true of chronic salbutamol treatment. Most significantly, the carvedilol-treated mice demonstrated an over 10-fold increase of the level of $\beta_2$-adrenergic receptors over the non-treated mice, demonstrating the efficacy of this β-adrenergic inverse agonist in increasing receptor levels upon chronic administration. Similarly, the nadolol-treated mice demonstrated a nearly eightfold increase of the level of receptors over the untreated methacholine-challenged asthmatic mice.

treated chronically with the $\beta_2$-adrenergic inverse agonist nadolol were used. The mice were sacrificed and the lungs excised. Then the lungs were fixed in 4% paraformaldehyde (45 min, 0° C.). After fixation, lungs were washed in PBS (60 min) and placed in increasing concentrations of sucrose (10% sucrose/5% glycine in PBS for 30 min; 20% sucrose/10% glycine in PBS for 30 min; 30% sucrose/15% glycine in PBS for 12 h at 4° C.). Lungs were embedded in OCT and 12-µm sections cut with a Tissue-Tek II cryostat. The sections were air dried and fixed with 4% paraformaldehyde for 15 min. After 3 washes in PBS, the slides were blocked with 5% milk in PBS for 1 h, and then incubated overnight with anti-$\beta_2$-adrenergic receptor antibody (1:200, Santa Cruz Biotechnology) in blocking solution. Slides were washed in PBS and incubated with secondary antibody (1:200, Cy3 goat anti-rabbit, 16 h at 4° C.). Control slides were incubated with antibody specific blocking peptide to demonstrate specificity of binding of the primary antibody. After washing with PBS, coverslips were mounted and viewed by epifluorescent microscopy.

Figure 4:
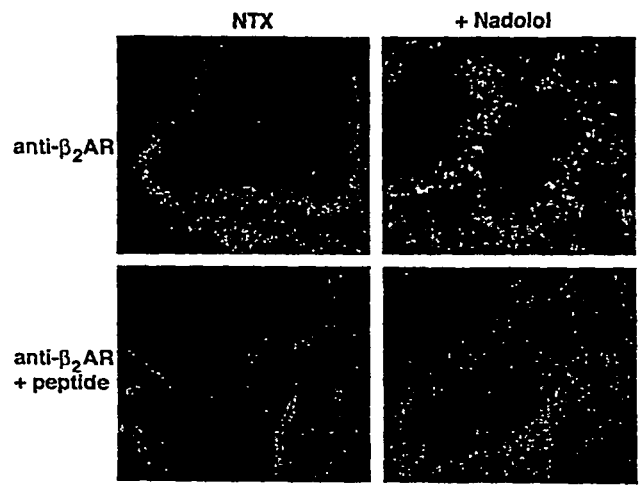
FIG. 4 is a series of epifluorescent photomicrographs showing an increase in β-adrenergic receptor density upon treatment with nadolol.

As shown in FIG. 4, labeling with anti-$\beta_2$-adrenergic receptor antibodies was considerably more intense in lungs from animals treated with nadolol than in lungs from untreated animals (A, control+antibody; B, control+antibody+blocking peptide; C, nadolol+antibody; D, nadolol+antibody+blocking peptide). Loss of this signaling upon incubation in the presence of the $\beta_2$-adrenergic receptor peptide demonstrates that this antibody is specifically binding the $\beta_2$-adrenergic receptor. This observation is consistent with the radioligand binding data of Example 2 and suggests that $\beta_2$-adrenergic receptors are effectively upregulated by chronic administration of $\beta_2$-adrenergic inverse agonist drugs.

Example 3

Effect of Combination of Carvedilol and Salbutamol on Airway Hyperresponsiveness The effect of combination therapy with carvedilol and salbutamol was compared to monotherapy with carvedilol alone on airway hyperresponsiveness in asthmatic mice.

Mice (Balb/cJ) aged 6 weeks were housed under specific pathogen-free conditions and fed a chicken ovalbumin-free diet. Mice were systemically sensitized with ovalbumin

TABLE 1

Determination of β-Adrenergic Receptor Density by Radioligand Binding

| | 15 Minutes | | 28 Days | |
|---|---|---|---|---|
| Treatment | $B_{max}$ | $K_D$ | $B_{max}$ | $K_D$ |
| Ctrl | 286.8 ± 88.02 | (107.9 ± 43.67) | 286.8 ± 88.02 | (107.9 ± 43.67) |
| NTX | 109.2 ± 9.72# | (193.6 ± 20.66) | 109.2 ± 9.72# | (193.6 ± 20.66) |
| Salbutamol | 256.5 ± 29.24* | (228.8 ± 33.07) | 97.0 ± 23.02 | (225.4 ± 41.79) |
| Alprenolol | 299.5 ± 12.19* | (453.6 ± 86.33) | 179.2 ± 53.05 | (290.9 ± 55.07) |
| Carvedilol | 86.3 ± 19.42 | (565.2 ± 192.8)* | 904.1 ± 43.46* | (1444.0 ± 202.0) |
| Nadolol | 181.9 ± 48.28 | (695.1 ± 286.3)* | 785.5 ± 154.8* | (1591.6 ± 335.0)* |

Example 3

Chronic Inverse Agonist Treatment Increases β-Adrenergic Receptor Numbers as Monitored by Immunohistochemistry For immunohistochemistry analysis of $\beta_2$-adrenergic receptor levels, non-drug-treated control mice and mice adsorbed to aluminum hydroxide. Mice were treated as follows: CAR/SAL 28D=for 28 days mice (n=6-12) were administered carvedilol (2400 ppm in animal chow) and salbutamol (subcutaneous delivery of 0.5 mg/kg/day in an Alzet #2400 osmotic minipump); NTX S/C=mice (n=6-12) no drug treatment for 28 days; CTRL=mice (n=6-12) no drug treatment for 28 days, not subsequently challenged; CARHD 28D=for 28 days mice (n=6-12) were administered carvedilol only (2400 ppm in animal chow); CARHD 28D SAL AC=for 28 days mice (n=6-12) were administered carvedilol (2400 ppm in animal chow) and 15 minutes prior to measuring airway hyperresponsiveness, salbutamol was administered at a dose of 1.2 mg/kg.

To measure airway hyperresponsiveness after 28 days, all mice except the CTRL (control) mice were challenged with ovalbumin and then all mice were anesthetized, tracheotomized, and connected to a Flexivent small animal ventilator to measure airway resistance ($R_{aw}$) by the forced oscillation technique. To induce airway constriction, a solution containing 150 μg/mL of methacholine was infused using a syringe infusion pump. The methacholine infusion was started at 0.008 mL/min and its rate was doubled stepwise up to a maximum 0.136 mL/min. Each methacholine dose was administered until a plateau was reached, during which data were sampled at 1-min intervals for 3-5 min and then averaged.

Figure 5A:
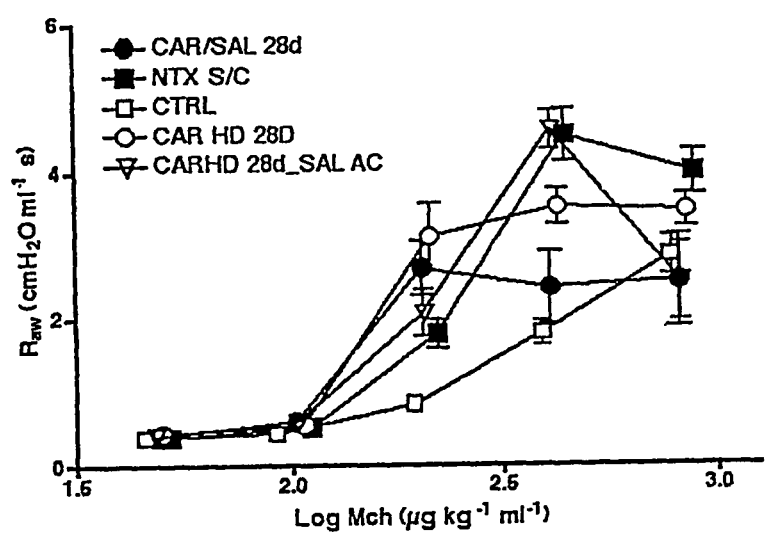
FIG. 5A is a graph showing the effect of combination therapy with carvedilol and salbutamol on airway hyperresponsiveness in asthmatic mice challenged with methacholine.

In FIG. 5A, at the highest dose of methacholine, both of the combination drug treatments were equally effective in preventing bronchoconstriction and not statistically significantly different from the control mice which were only challenged with saline solution. The carvedilol monotherapy resulted in higher bronchoconstriction than these treatments but less than the non-drug treated sensitized and challenged (NTX S/C) mice. Thus, the combination therapy of $\beta_2$-adrenergic inverse agonist and agonist with the agonist administered either chronically or acutely is effective at ameliorating airway hyperresponsiveness to allergen and methacholine challenge and is an improvement over the monotherapy of the β2-adrenergic inverse agonist alone.

Figure 5B:
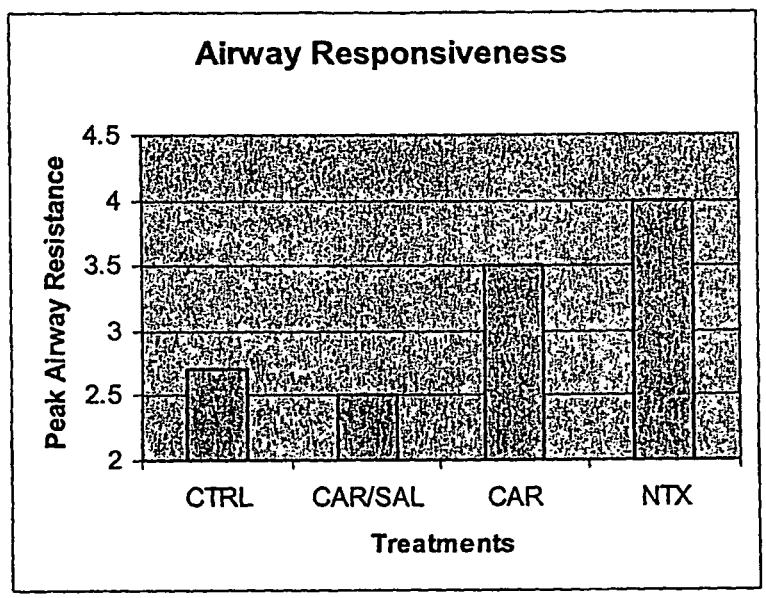
FIG. 5B is a summary graph showing the results presented in FIG. 5A.

This data is summarized in FIG. 5B, which shows that the combination of carvedilol and salbutamol is the most effective in reducing airway hyperresponsiveness of the treatments for which the results are shown in FIG. 5A. This indicates the effectiveness of the use of combination therapy of $\beta_2$-adrenergic inverse agonist and agonist.

Example 4

Effect of Combination Therapy with Aminophylline on Acute Airway Effects of Nadolol Mice were sensitized to the allergen ovalbumin as described in Example 1. Mice were then challenged with allergen and then subjected to methacholine-induced bronchoconstriction challenge, non-drug treated, NTX S/C, or pretreated with nadolol at 0.72 mg/kg i.p. for 15 minutes prior to methacholine challenge (nadolol acute treatment).

At time point 1 (time=−10 min) baseline airway resistance of the mice was determined. At time point 2 (time=−5 min) methacholine was infused into mice to reach their $EC_{70}$. At time point 3 (time=0 min) aminophylline was administered i.p. at a dose of 100 mg/kg.

Figure 6:
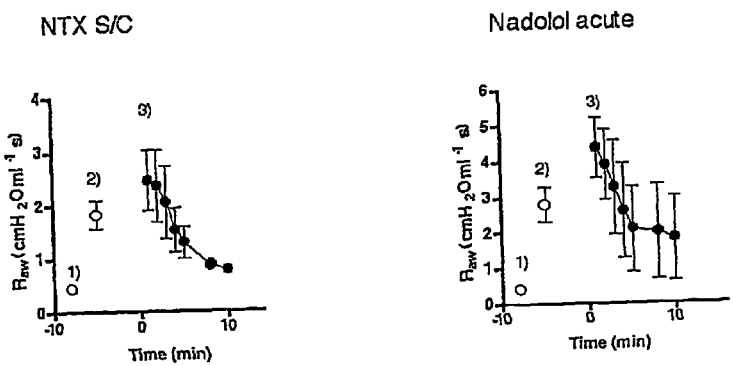
FIG. 6 is a graph showing the effect of acute combination therapy with nadolol and aminophylline on airway hyperresponsiveness in asthmatic mice challenged with methacholine.

In FIG. 6, pretreatment of mice with nadolol resulted in the same baseline airway resistance as non-drug treated sensitized and allergen-challenged mice. However, upon methacholine challenge, the nadolol-treated mice exhibited a much higher airway resistance of ~4.5 versus 2.5 units. Upon administration of aminophylline, there was a significant and sustained drop in airway resistance in both the untreated and the nadolol-treated mice.

Z. Callaerts-Vegh et al., "Effects of Acute and Chronic Administration of β-Adrenoceptor Ligands on Airway Function in a Murine Model of Asthma," *Proc. Natl. Acad. Sci. USA* 101: 49484953 (2004), have shown that while nadolol administered chronically prevents airway hyperresponsiveness in the same mouse asthma model, nadolol administered acutely worsens airway hyperresponsiveness. These data demonstrate that the addition of the methylxanthine aminophylline can alleviate the acute effects on airway hyperresponsiveness of nadolol administration. This is beneficial in that the opportunity exists for asthma subjects to take nadolol chronically to prevent bronchoconstriction. These subjects then can co-administer a methylxanthine such as aminophylline to prevent the acute detrimental effects of nadolol.

Example 5

Effect of Treatment with Salbutamol or Nadolol on the Ratio of Phospholipase C to Actin in Cultured Tracheal Smooth Muscle Cells Cultured tracheal smooth muscle cells were obtained from mice exposed to the following treatments: NS/NC=nonasthmatic, non-challenged mice; S/C=asthmatic mice; Sal.Ac=asthmatic mice, acute salbutamol treatment; Sal.Ch=asthmatic mice, chronic salbutamol treatment; Nad.Ac=asthmatic mice, acute nadolol high dose treatment; and Nad.Ch=asthmatic mice, chronic nadolol high dose treatment.

After airway function experiments, the trachea were surgically removed from anesthetized mice that had been treated with drugs or vehicle. The trachea was minced and the cells plated and grown in culture. The smooth muscle cells grow faster and take over the culture dish. The cells were grown in medium which contained the drugs used in the treatment or vehicle controls. Phospholipase C (PLC-$\beta_1$) was determined by immunoblotting with an antibody specific for the enzyme. Actin was used as a loading control and the amount of PLC-$\beta_1$ was expressed as a ratio to actin.

The phospholipase C protein level was measured in these cultured cells and compared with the level of the structural protein actin as a baseline. The enzyme phospholipase C plays a key role in the pathway leading to asthmatic symptoms, as it cleaves a phosphodiester bond in membrane phospholipids, resulting in the formation of a 1,2-diglyceride. Arachidonate is then released from the diglyceride by the sequential actions of diglyceride lipase and monoglyceride lipase. Once released, a portion of the arachidonate is metabolized rapidly, leading to oxygenated products, including eicosanoids such as prostaglandins. Thus, any treatment that can inhibit phospholipase C activity is relevant for the treatment of asthma.

Figure 7:
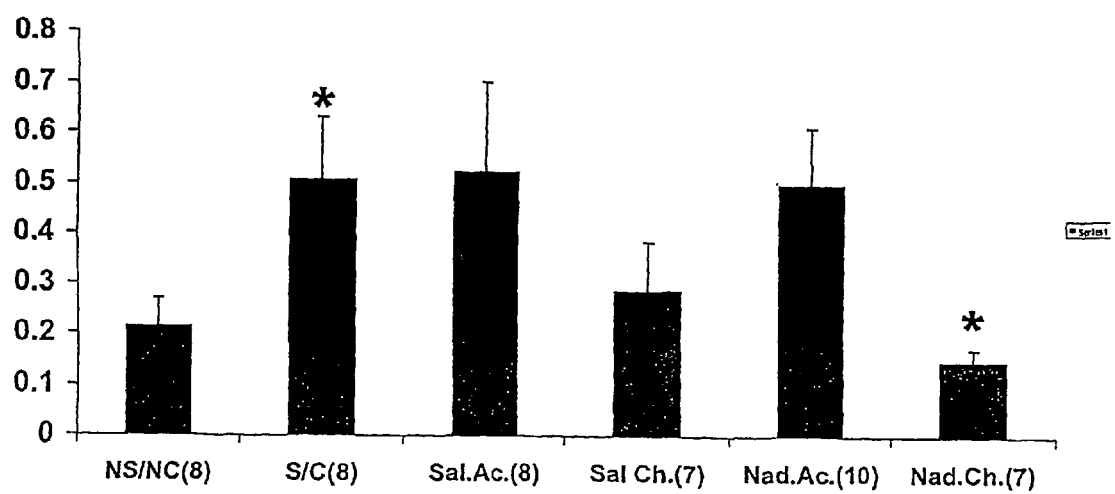
FIG. 7 is a graph showing the ratio of phospholipase C to actin in mice treated with various treatments, including long-term nadolol administration, to show that long-term nadolol administration decreases the activity of phospholipase C.

The results are shown in FIG. 7. The results shown in FIG. 7 indicate that chronic administration of nadolol significantly decreases the activity of phospholipase C. This indicates that such chronic administration of nadolol is effective against asthma and prevents activation of some of the mechanisms that lead to the symptoms of asthma.

Example 6

Effect of β-Adrenergic Receptor Drugs at Low and High Doses on Airway Resistance For these experiments, salbutamol was used for chronic administration at 0.5 mg/kg/day with a minipump and for acute administration at 0.15 mg/kg by i.v. bolus 15 minutes prior to challenge. Alprenolol was used at a high dose of 7200 ppm in chow or at a low dose of 720 ppm in chow. Carvedilol was used at a high dose of 2400 ppm in chow or at a low dose of 720 ppm in chow. Nadolol was used at a high dose of 250 ppm in chow or at a low dose of 25 ppm in chow. Nadolol was also tested at 1 ppm in chow and these results were identical to the untreated mice.

Figure 8:
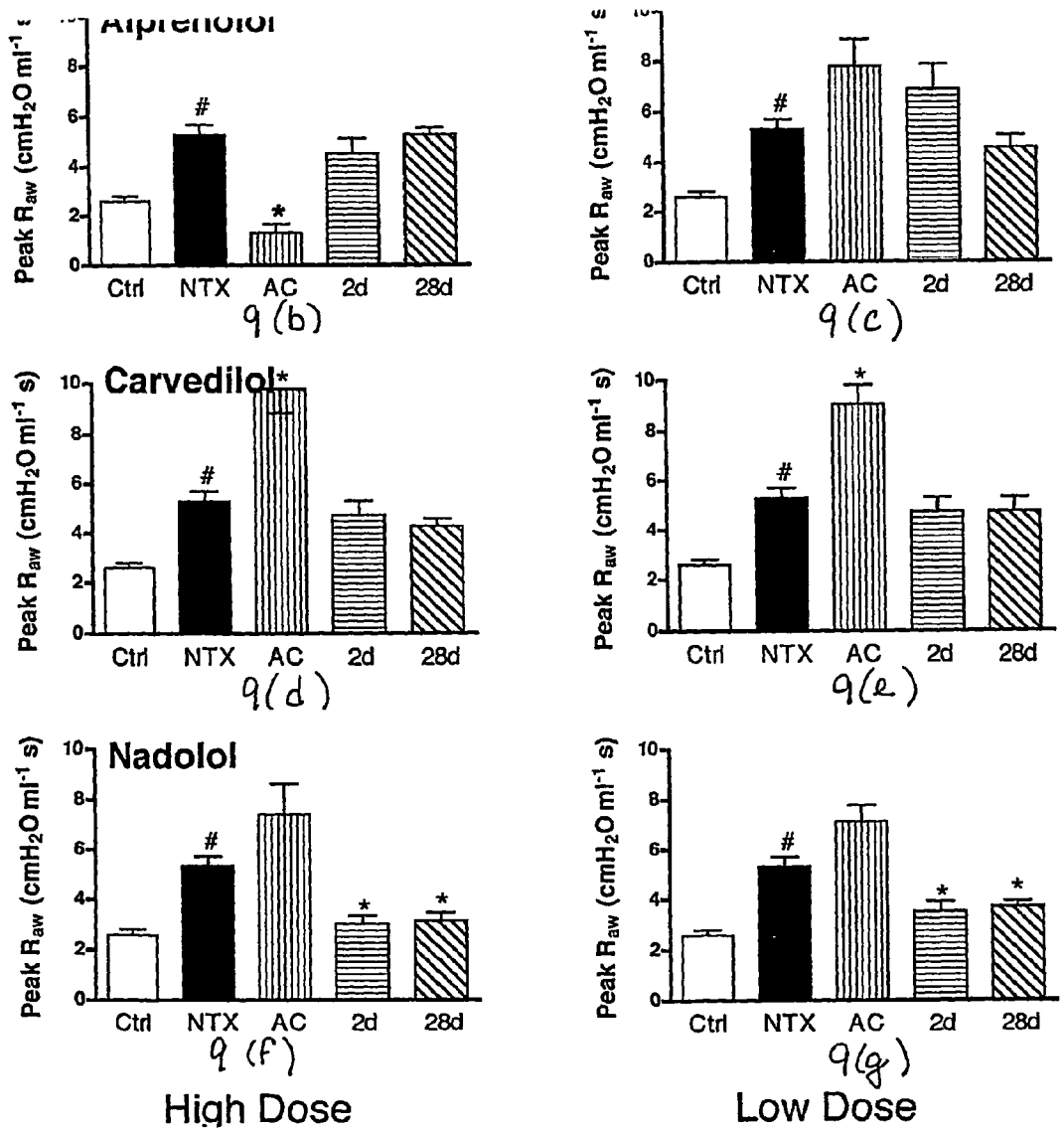
FIG. 8A is a graph showing the effects of salbutamol upon airway hyperresponsiveness.
FIG. 8B is a graph showing the effects of high-dose alprenolol upon airway hyperresponsiveness.
FIG. 8C is a graph showing the effects of low-dose alprenolol upon airway hyperresponsiveness.
FIG. 8D is a graph showing the effects of high-dose carvedilol upon airway hyperresponsiveness.
FIG. 8E is a graph showing the effects of low-dose carvedilol upon airway hyperresponsiveness.
FIG. 8F is a graph showing the effects of high-dose nadolol upon airway hyperresponsiveness.
FIG. 8G is a graph showing the effects of low-dose nadolol upon airway hyperresponsiveness.

The results are shown in FIGS. 8A (salbutamol); 8B (high-dose alprenolol); 8C (low-dose alprenolol); 8D (high-dose carvedilol); 8E (low-dose carvedilol); 8F (high-dose nadolol); and 8G (low-dose nadolol). In these diagrams, Ctrl=control mice, non-asthmatic, non-drug treated; NTX=asthmatic mice, non-drug treated; AC=acute administration; 2d=chronic administration for 2 days; 28d=chronic administration for 28 days. The airway resistance ($R_{aw}$) is plotted as cm $H_2O$ $ml^{-1}$ s. The data particularly shows the effect of the β-adrenergic inverse agonists carvedilol and nadolol in providing protection from airway hyperresponsiveness with chronic administration.

Example 7

Correlation of Decrease in Airway Resistance with Upregulation of β-Adrenergic Receptor Density The correlation of the decrease in airway resistance with the upregulation of β-adrenergic receptor density for three different periods of administration of salbutamol, alprenolol, carvedilol, and nadolol is shown in Table 2. The periods of administration of the agents are 15 minutes, 2 days, and 28 days. Only the inverse agonists carvedilol and nadolol showed an increase in β-adrenergic receptor density at periods longer than 15 minutes; carvedilol showed an increase in receptor density at 28 days, while nadolol showed an increase in receptor density at both 2 days and 28 days. There was an exact correlation between the decrease of airway resistance ($R_{aw}$) and the increase in receptor density. This strongly supports the concept of combination therapy, such as with an inverse agonist and an agonist.

TABLE 2

Correlation of Decrease In Airway Resistance With Upregulation of $β_2$-Adrenergic Receptor Density

| | 15 minutes | | 2 days | | 28 days | |
|---|---|---|---|---|---|---|
| | Decreased $R_{aw}$ | Increased $β_2$AR density | Decreased $R_{aw}$ | Increased $β_2$AR density | Decreased $R_{aw}$ | Increased $β_2$AR density |
| Salbutamol | yes | yes | no | no | no | no |
| Alprenolol | yes | yes | no | no | no | no |
| Carvedilol | no | no | no | no | yes | yes |
| Nadolol | no | no | yes | yes | yes | yes |

Example 8

Figure 9A:
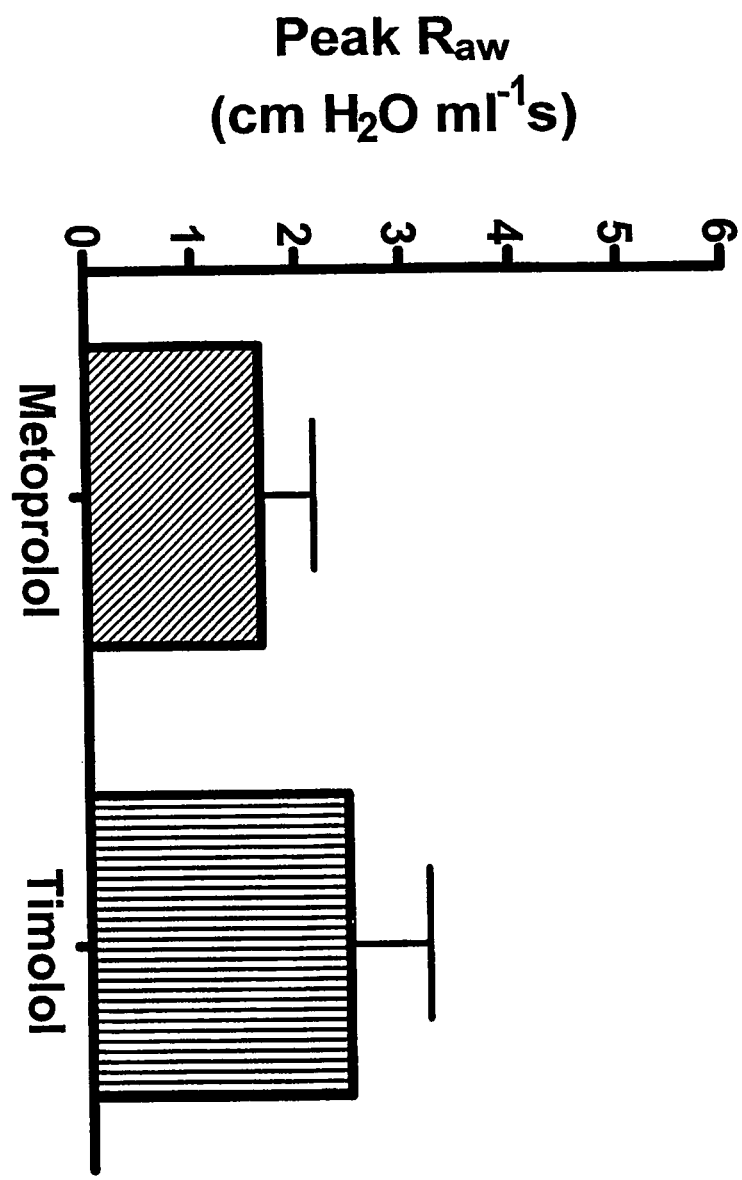
FIG. 9 is a set of graphs showing the effects of long-term dosage of metoprolol and timolol upon airway hyperresponsiveness in asthmatic mice: (A) experimental results with metoprolol and timolol; (B) historical controls with non-challenged mice (Ctrl) and with challenged mice with no treatment (NTX).
Figure 9B:
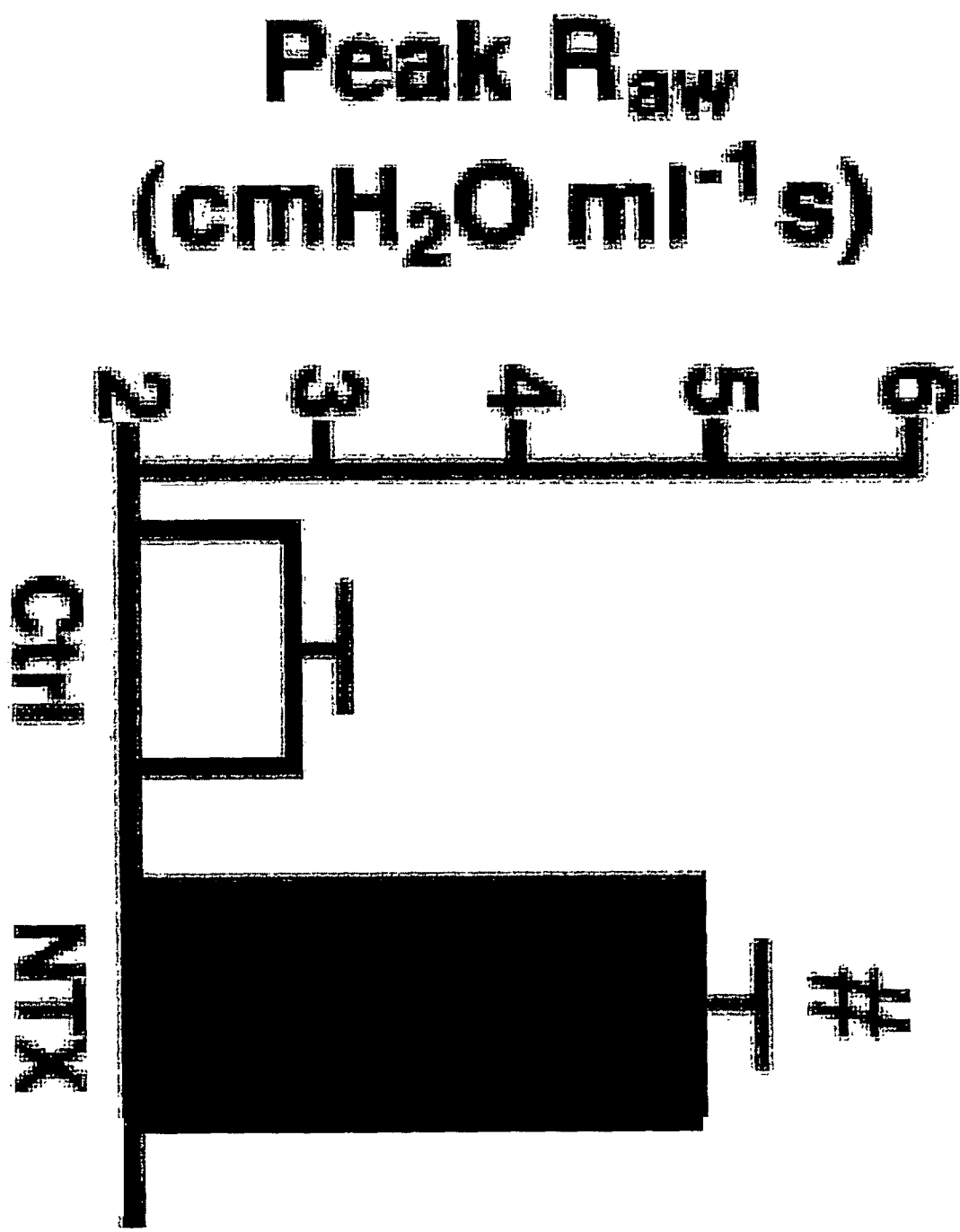

Effects of Chronic Treatment with Metoprolol and Timolol on Airway Hyperresponsiveness in Asthmatic Mice The protocols of Example 1 were followed for two additional inverse agonists, metoprolol (dosage of 20 mg/kg administered 3× daily via subcutaneous injection for 7 days) and timolol (dosage of 20 mg/kg in chow for 7 days), using asthmatic mice and methacholine challenge as in Example 1. Airway resistance ($R_{aw}$) was measured as in Example 1. The results for metoprolol and timolol are shown in FIG. 9A. The results were compared to historical controls as shown in FIG. 9B: Ctrl, no drug treatment, no challenge with methacholine; NTX, no drug treatment, challenged with methacholine. The results indicate that chronic treatment with both metoprolol and timolol are effective in reducing airway hyperresponsiveness in asthmatic mice.

ADVANTAGES OF THE INVENTION

The present invention provides a improved method of treating chronic pulmonary airway diseases such as asthma, emphysema, and chronic obstructive pulmonary diseases and avoids the tolerance or tachyphylaxis that often is the consequence of conventional therapy with β-adrenergic agonists. The use of inverse agonists, in essence, forces the body to respond by improving its own signaling mechanisms to counter the pulmonary airway disease. Accordingly, compositions and methods that employ inverse agonists have broad potential for treating such diseases and conditions without the induction of tolerance. This promises superior long-term results in the treatment of such conditions without interfering with short-term acute therapy.

The inventions illustratively described herein can suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the future shown and described or any portion thereof, and it is recognized that various modifications are possible within the scope of the invention claimed. Thus, it should be understood that although the present invention has been specifically disclosed by preferred embodiments and optional features, modification and variation of the inventions herein disclosed can be resorted by those skilled in the art, and that such modifications and variations are considered to be within the scope of the inventions disclosed herein. The inventions have been described broadly and generically herein. Each of the narrower species and subgeneric groupings falling within the scope of the generic disclosure also form part of these inventions. This includes the generic description of each invention with a proviso or negative limitation removing any subject matter from the genus, regardless of whether or not the excised materials specifically resided therein.

In addition, where features or aspects of an invention are described in terms of the Markush group, those schooled in the art will recognize that the invention is also thereby described in terms of any individual member or subgroup of members of the Markush group. It is also to be understood that the above description is intended to be illustrative and not restrictive. Many embodiments will be apparent to those of in the art upon reviewing the above description. The scope of the invention should therefore, be determined not with reference to the above description, but should instead be determined with reference to the appended claims, along with the full scope of equivalents to which such claims are entitled. The disclosures of all articles and references, including patent publications, are incorporated herein by reference.

I claim:

1. A method for treatment of pulmonary airway disease in a subject suffering from pulmonary airway disease comprising chronically administering a therapeutically effective amount of a β-adrenergic inverse agonist to the subject to treat the pulmonary airway disease by action of inverse agonism to promote long-term upregulation of the population of β-adrenergic receptors upon chronic administration of the β-adrenergic inverse agonist, wherein the β-adrenergic inverse agonist exhibits inverse agonist activity at the $\beta_2$ receptor of bronchial tissue, wherein the β-adrenergic inverse agonist is selected from the group consisting of nadolol, bupranolol, butoxamine, carazolol, ICI-118,551, levobunolol, metoprolol, and timolol, and wherein such chronic administration requires increasing dosages over time.

2. The method of claim 1 wherein the β-adrenergic inverse agonist is nadolol.

3. The method of claim 1 wherein the β-adrenergic inverse agonist is administered by a route selected from the group consisting of oral, sustained-release oral, parenteral, sublingual, buccal, insufflation, and inhalation.

4. The method of claim 3 wherein the β-adrenergic inverse agonist is administered by the sustained-release oral route.

5. The method of claim 1 wherein the pulmonary airway disease is selected from the group consisting of asthma, bronchiectasis, bronchitis, chronic obstructive pulmonary disease, Churg-Strauss syndrome, pulmonary sequelae of cystic fibrosis, emphysema, allergic rhinitis, and pneumonia.

6. The method of claim 5 wherein the pulmonary airway disease is asthma.

7. The method of claim 5 wherein the pulmonary airway disease is chronic obstructive pulmonary disease.

8. The method of claim 5 wherein the pulmonary airway disease is emphysema.

9. The method of claim 1 wherein the β-adrenergic inverse agonist is administered over time in a series of graduated doses starting with the lowest dose and increasing to the highest dose, wherein such graduated doses are determined by determination of the increase of receptor density.

10. The method of claim 9 wherein, when the highest dose is reached, the β-adrenergic inverse agonist continues to be administered at that dose.

11. The method of claim 1 further comprising administering a therapeutically effective amount of an additional agent selected from the group consisting of: a $\beta_2$-selective adrenergic agonist; a steroid; an anticholinergic drug; a xanthine compound; an anti-IgE antibody; a leukotriene modifier; and a phosphodiesterase inhibitor in order to treat the pulmonary airway disease by action of inverse agonism to promote long-term upregulation of the population of β-adrenergic receptors upon chronic administration of the β-adrenergic inverse agonist, wherein the β-adrenergic inverse agonist exhibits inverse activity at the $\beta_2$ receptor of bronchial tissue.

12. The method of claim 11 wherein the additional agent is a $\beta_2$-selective adrenergic agonist and the $\beta_2$-selective adrenergic agonist is selected from the group consisting of albuterol, bitolterol, clenbuterol, clorprenaline, dobutamine, fenoterol, formoterol, isoetharine, isoprenaline, levabuterol, mabuterol, metaproterenol, pirbuterol, ritodrine, salbutamol, salmeterol, terbutaline, and the salts thereof.

13. The method of claim 11 wherein the additional agent is a steroid and wherein the steroid is selected from the group consisting of beclomethasone, budenoside, ciclesonide, flunisolide, fluticasone, methylprednisolone, prednisolone, prednisone, and triamcinolone, and the salts thereof.

14. The method of claim 11 wherein the additional agent is an anticholinergic drug and wherein the anticholinergic drug is selected from the group consisting of ipratropium bromide, tiotropium bromide, and oxitropium bromide, and the salts thereof.

15. The method of claim 11 wherein the additional agent is a xanthine compound and wherein the xanthine compound is selected from the group consisting of theophylline, extended-release theophylline, aminophylline, theobromine, enprofylline, diprophylline, isbufylline, choline theophyllinate, albifylline, arofylline, bamifylline and caffeine.

16. The method of claim 11 wherein the additional agent is an anti-IgE antibody and wherein the anti-IgE antibody is a monoclonal antibody or a genetically engineered antibody that is derived from a monoclonal antibody.

17. The method of claim 11 wherein the additional agent is a leukotriene modifier and wherein the leukotriene modifier is selected from the group consisting of ibudilast, montelukast, pranlukast, and zafirlukast, and the salts thereof.

18. The method of claim 11 wherein the additional agent is a phosphodiesterase IV inhibitor and wherein the phosphodiesterase IV inhibitor is selected from the group consisting of roflumilast and cilomilast, and the salts thereof.

* * * * *